US008221993B2

(12) United States Patent
Nakamura et al.

(10) Patent No.: US 8,221,993 B2
(45) Date of Patent: *Jul. 17, 2012

(54) METHODS OF DETECTING METHYL TRANSFERASE ACTIVITY AND METHODS OF SCREENING FOR METHYL TRANSFERASE ACTIVITY MODULATORS

(75) Inventors: Yusuke Nakamura, Yokohama (JP); Yoichi Furukawa, Kawasaki (JP)

(73) Assignee: Onco Therapy Science, Inc., Kanagawa (JP)

( * ) Notice: Subject to any disclaimer, the term of this patent is extended or adjusted under 35 U.S.C. 154(b) by 1041 days.

This patent is subject to a terminal disclaimer.

(21) Appl. No.: 10/586,987

(22) PCT Filed: Jan. 21, 2005

(86) PCT No.: PCT/JP2005/001172
§ 371 (c)(1),
(2), (4) Date: Oct. 15, 2008

(87) PCT Pub. No.: WO2005/071102
PCT Pub. Date: Aug. 4, 2005

(65) Prior Publication Data
US 2009/0035303 A1 Feb. 5, 2009

Related U.S. Application Data

(60) Provisional application No. 60/538,658, filed on Jan. 23, 2004.

(51) Int. Cl.
*C12N 9/10* (2006.01)
*C12Q 1/48* (2006.01)
*G01N 33/573* (2006.01)
(52) U.S. Cl. ............... 435/7.4; 435/4; 435/15; 435/193
(58) Field of Classification Search ............... 435/4, 7.4, 435/15, 193
See application file for complete search history.

(56) References Cited

U.S. PATENT DOCUMENTS

| 6,955,905 | B2* | 10/2005 | Huang | ........................... 435/193 |
|---|---|---|---|---|
| 2004/0235018 | A1 | 11/2004 | Nakamura et al. | |
| 2009/0142344 | A1 | 6/2009 | Nakamura et al. | |
| 2009/0191181 | A1 | 7/2009 | Nakamura et al. | |
| 2010/0184088 | A1 | 7/2010 | Nakatsuru | |
| 2010/0248240 | A1 | 9/2010 | Nakamura et al. | |

FOREIGN PATENT DOCUMENTS

| JP | 2004/264294 A | 9/2004 |
|---|---|---|
| WO | WO 98/33904 A2 | 8/1998 |
| WO | WO 98/39904 A3 | 8/1998 |
| WO | WO 00/17355 A2 | 3/2000 |
| WO | WO 00/44900 A2 | 8/2000 |
| WO | WO 02/059377 A2 | 8/2002 |
| WO | WO 02/092002 A2 | 11/2002 |
| WO | WO 03/010180 A1 | 2/2003 |
| WO | WO 03/027143 A2 | 4/2003 |
| WO | WO 2004/076623 A2 | 9/2004 |
| WO | WO 2008/152816 A1 | 12/2008 |

OTHER PUBLICATIONS

Santos-Rosa, H., et al., Nature, 419, 407-411, 2002.*
Reeck, G., et al., "'Homology' in Proteins and Nucleic Acids: A Terminology Muddle and a Way Out of It," *Cell*, vol. 50(5), p. 667 (Aug. 28, 1987).
Firestein, R., et al., "Set Domain-Dependent Regulation of Transcriptional Silencing and Growth Control by SUV39H1, a Mammalian Ortholog of *Drosophila* Su(var)3-9," *Molecular and Cellular Biology*, vol. 20(7), pp. 4900-4909 (Jul. 2000).
Hamamoto, et al., "Isolation and characterization of ZNFN3A1, a novel gene whose expression is frequently up-regulated in hepatocellular carcinoma," *Jpn J Cancer Res* (Proceeding Sixtieth Annual Meeting of the Japanese Cancer Association), vol. 92 (Supplement), p. 117, abstract 208 (2001).
Kato, T. et al., "Isolation of a novel human gene, DDEFL1 (Development and Differentiation Enhancing Factor-Like 1), as a molecular target of HCC," *Jpn J Cancer Res* (Proceedings Sixty-First Annual Meeting of the Japanese Cancer Association), vol. 93 (Supplement), p. 78, abstract 2033 (2002).
Mao, Y., et al., Geneseq Accession No. AAG66728, 1 pp (Nov. 26, 2001).
Nozaki, T., et al., "Involvement of the VEGFR-1 in prostatic carcinogenesis," *The American Association for Cancer Research/AACR*, vol. 45, p. 213, abstract #934 (2004).
Okabe, H., et al., "Genome-wide Analysis of Gene Expression in Human Hepatocellular Carcinomas Using cDNA Microarray: Identification of Genes Involved in Viral Carcinogenesis and Tumor Progression," *Cancer Research*, vol. 61(5), pp. 2129-2137 (Mar. 1, 2001).
Rozovskaia, T., et al., "Self-association of the SET domains of human ALL-1 and of *Drosophila* TRITHORAX and ASH1 proteins," *Oncogene*, vol. 19(3), pp. 351-357 (Jan. 20, 2000).
Strausberg, R. et al., "Generation and initial analysis of more than 15,000 full-length human and mouse cDNA sequences," *PNAS*, vol. 99(26), pp. 16899-16903 (Dec. 24, 2002, Epub Dec. 11, 2002).
Strausberg, R., et al., "*Homo sapiens* SET and MYND domain containing 3, mRNA (cDNA clone MGC:32757 IMAGE:4334047), complete cds," GenBank Accession No. BC031010, 3 pgs. (Jun. 13, 2002).
U.S. Appl. No. 13/076,137, filed Mar. 30, 2011, 53 pgs.
U.S. Appl. No. 13/092,770, filed Apr. 22, 2011, 59 pgs.
Du, Yong, et al.; "Hypermethylation in Human Cancers of the *RIZ1* Tumor Suppressor Gene, a Member of a Histone/Protein Methyltransferase Superfamily;" *Cancer Research*; Nov. 15, 2001; pp. 8094-8099; 61:22.
Echeverri, Chris, et al.; "siRNA Design: It's All in the Algorithm;" Ambion.com; *TechNotes*; 11:3; [http://www.ambion.com/techlib/tn/113/14.html], 2004.

(Continued)

*Primary Examiner* — Alana Harris Dent
*Assistant Examiner* — Anne Holleran
(74) *Attorney, Agent, or Firm* — Kilpatrick Townsend & Stockton LLP

(57) ABSTRACT

The invention features a method for determining methyl transferase activity of a polypeptide and screening for modulators of methyl transferase activity. The invention further provides a method or pharmaceutical composition for prevention or treating of colorectal cancer or hepatocellular carcinoma using the modulator.

16 Claims, 9 Drawing Sheets

OTHER PUBLICATIONS

Fu, Tie-Bo and John Taylor; "The RNAs of Hepatitis Delta Virus Are Copied by RNA Polymerase II in Nuclear Homogenates;" *Journal of Virology*; Dec. 1993; pp. 6965-6972; 67:12.

Hamamoto, Ryuji, et al.; "ZNFN3A1, a novel gene that promotes growth in hepatocellular carcinoma;" *Proceedings of the Annual Meeting of the American Association for Cancer Research*; Mar. 2002; 43; 13; #63.

Hamamoto, Ryuji, et al.; "SMYD3 encodes a histone methyltransferase involved in the proliferation of cancer cells;" *Nature Cell Biology*; Aug. 2004; pp. 731-740; 6:8.

Li, W. B., et al.; "Full-length cDNA libraries and normalization;" EMBL Accession No. AL557360; Feb. 11, 2001.

Lüking, Angelika, et al.; "The Protein Family of RNA Helicases;" *Critical Reviews in Biochemistry and Molecular Biology*; 1998; pp. 259-296; 33:4.

Nakajima, Tohsihiro, et al.; "RNA Helicase a Mediates Assocation of CBP with RNA Polymerase II;" *Cell*; Sep. 19, 1997; pp. 1107-1112; 90:6.

Rea, Stephen, et al.; "Regulation of chromatin structure by site-specific histone H3 methyltransferases;" *Nature*; Aug. 10, 2000; pp. 593-599; 406:6796.

Stockand, James D., et al.; "S-Adenosyl-L-homocysteine Hydrolase Regulates Aldosterone-induced $Na^+$ Transport;" *The Journal of Biological Chemistry*; Feb. 5, 1999; pp. 3842-3850; 274:6.

Strahl, Brian D., et al.; "Methylation of histone H3 at lysine 4 is highly conserved and correlates with transcriptionally active nuclei in *Tetrahymena*;" *Proceedings of the National Academy of Sciences of the United States of America* (*PNAS*); Dec. 21, 1999; pp. 14967-14972; 96:26.

Sugano, Sumio, et al.; "NEDO human cDNA sequencing project;" EMBL Accession No. AK024733; Sep. 29, 2000.

GeneCards; *SMYD3*; [http://www.genecards.org/cgi-bin/carddisp.pl?gene=SMYD3&search=gc01m242239&suff=txt]; Jun. 16, 2006.

GENESEQ; Accession No. RS10672134; Nov. 13, 2003.

* cited by examiner

```
                NHSC XX N                                              GEEL XXX Y                    Cys Rich Region
ZNFN3A1     202 SLLLNHSCDPNCGSI VFNQP--------HLLLRQVRDI EVGEELTI CYLDMLMTSEEFRKQLRDQYCFECDC---FRQQTQ 269
SUV39H1         HFVNHSCDPNL QVYNVFI DNLDERLPRI AFFATRTI PAGEELTFDYNMQVDP-(20)--PKKRVRI ECKCGTESCRKY
SET7/9          RLI NHSkCCGNCQTKLHDI DG---VPHLI LI ASRDI AAGEELLYDYGDRSKASI EAHPWLKHLDGSGTDYKDDDDK*
MLL1            RFI NHSCEPNQYSRVIN I DG---QKH VI FAMFRKI YRGEELTYDYKFPI ED---------ASNKLPNCGAKKQRKF
                   *        .  . .     . .    *   :    .  | . .   *. . .|. . .:*| .. | . :   *  .
Blast consensus RFI NHSCTPNCEASPI EVNG----I FKI SI YAI RDI KAGEELTYDYGPSLEDNRE---LKKLLEKRWGQACQEDRCSHT
```

(b)

| UV-radiation | 0 min. | 5 min. | 10 min. |
|---|---|---|---|
| Mock | | | |
| ZNFN3A1 | | | |
| ZNFN3A1-ΔEEL | | | |
| ZNFN3A1-ΔNHSC | | | |

Coomassie
Fluorogram (c)

|  |  |  |  |  |
|---|---|---|---|---|
| Mock | + | − | − | − |
| ZNFN3A1 | − | + | − | − |
| SET7 | − | − | + | − |
| Hsp90α | − | − | − | + |

H3, H2B, H2A, H4
H3

Coomassie
Fluorogram

Fig. 2
a
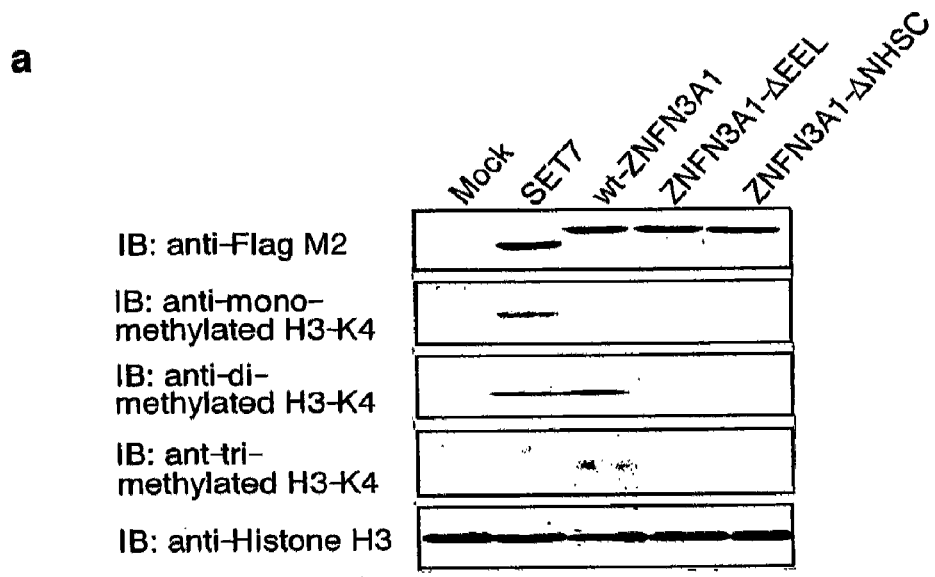
b
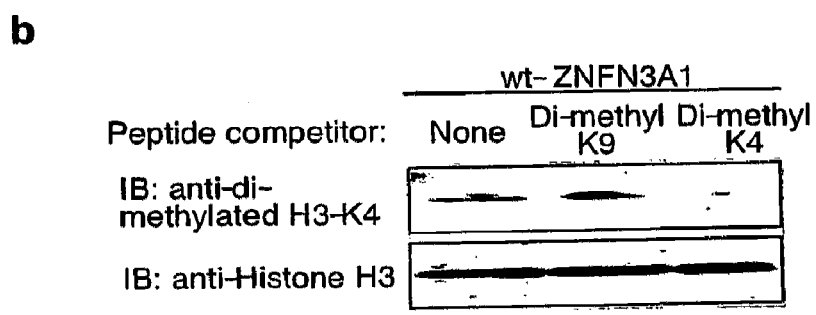
c
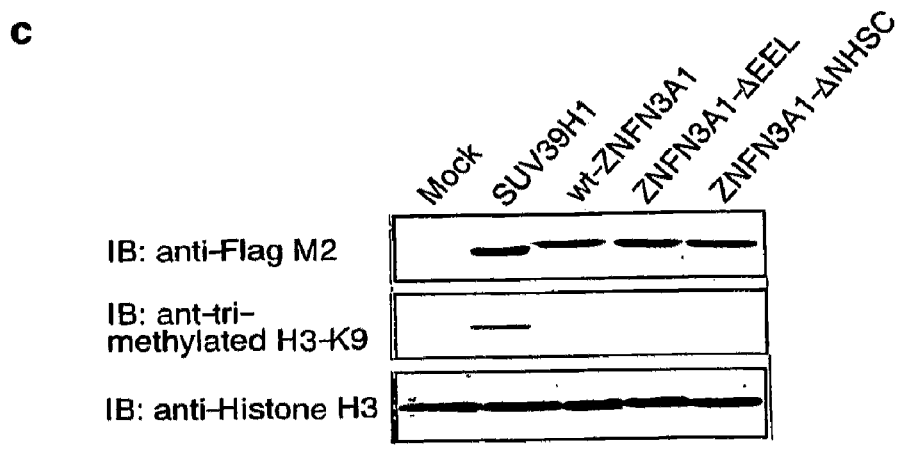

Fig. 4
(a) HEK293 cells
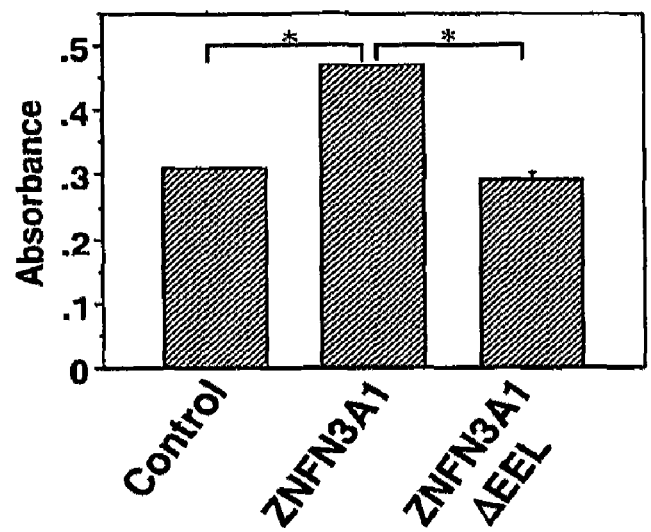
(b) HCT116 cells
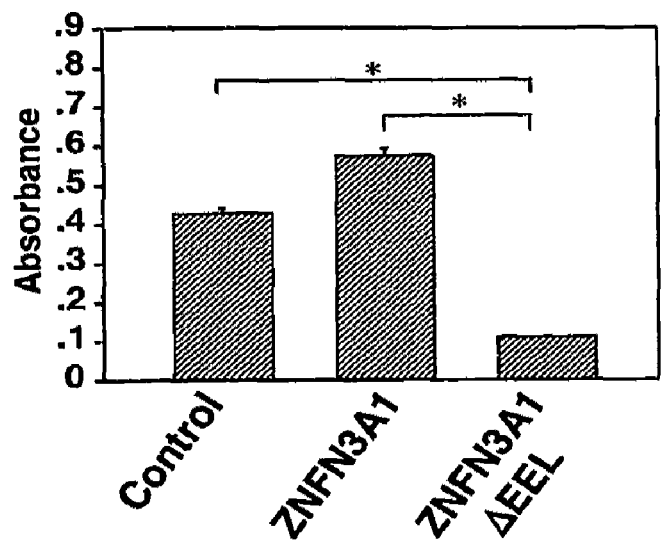

Fig. 6
(a)
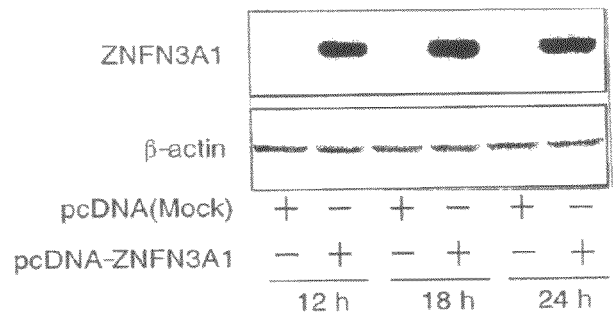
(b)
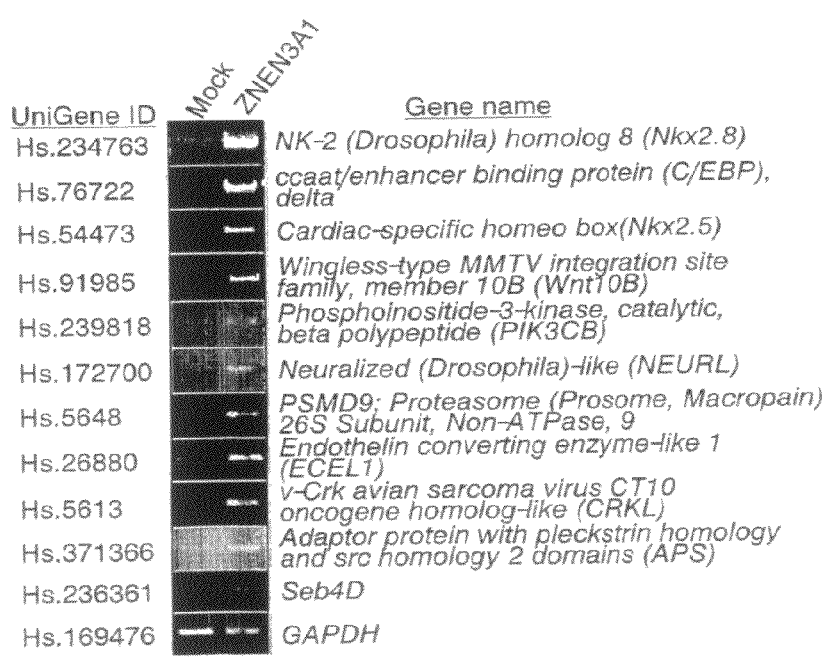

Fig. 7
(a)
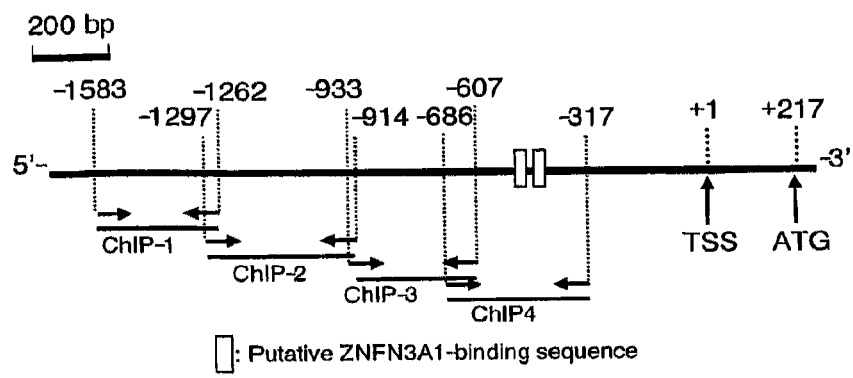
(b)
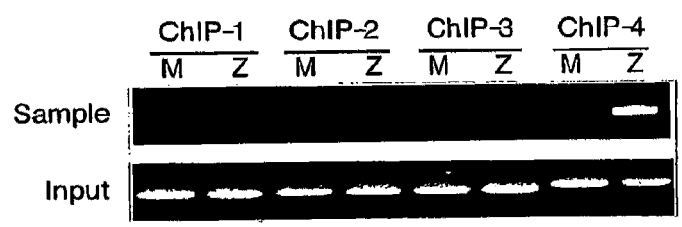
(c)
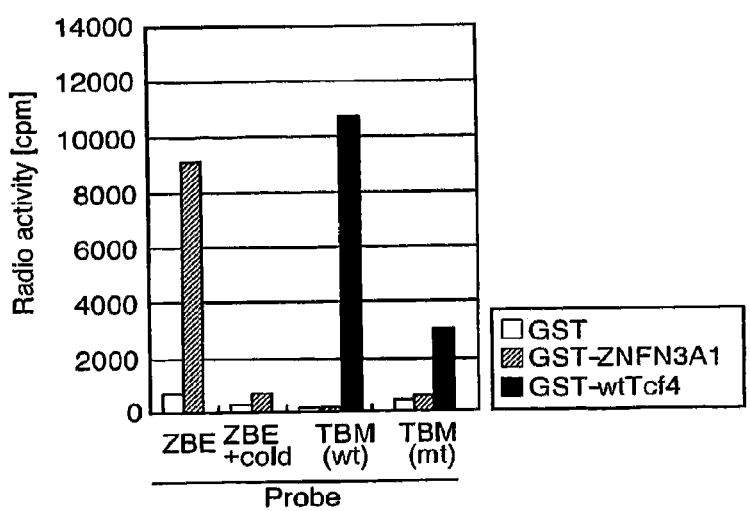

Fig. 7
(d)
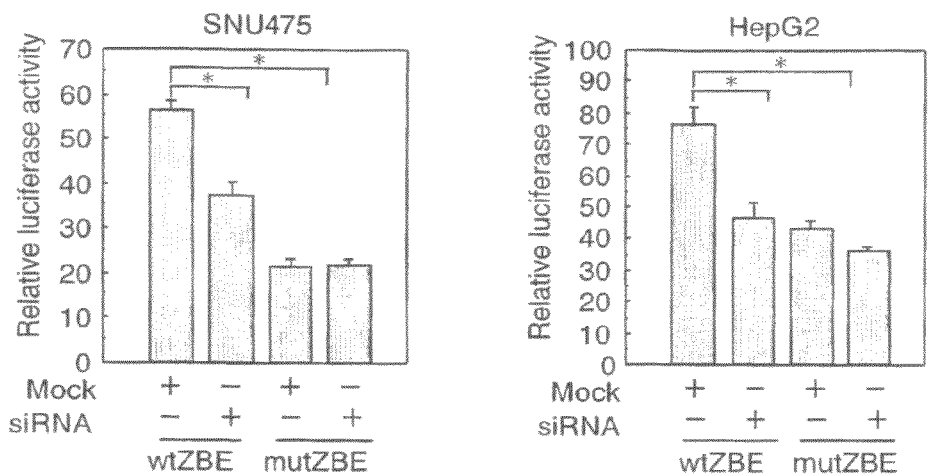
(e)
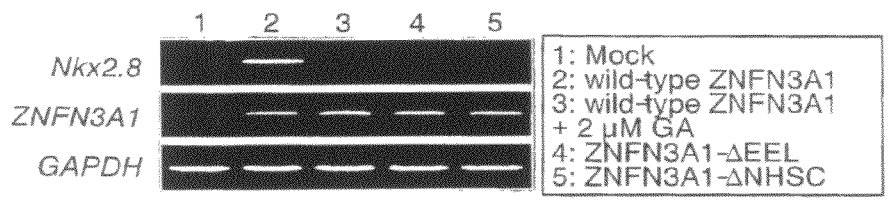
1: Mock
2: wild-type ZNFN3A1
3: wild-type ZNFN3A1 + 2 μM GA
4: ZNFN3A1-ΔEEL
5: ZNFN3A1-ΔNHSC
(f)
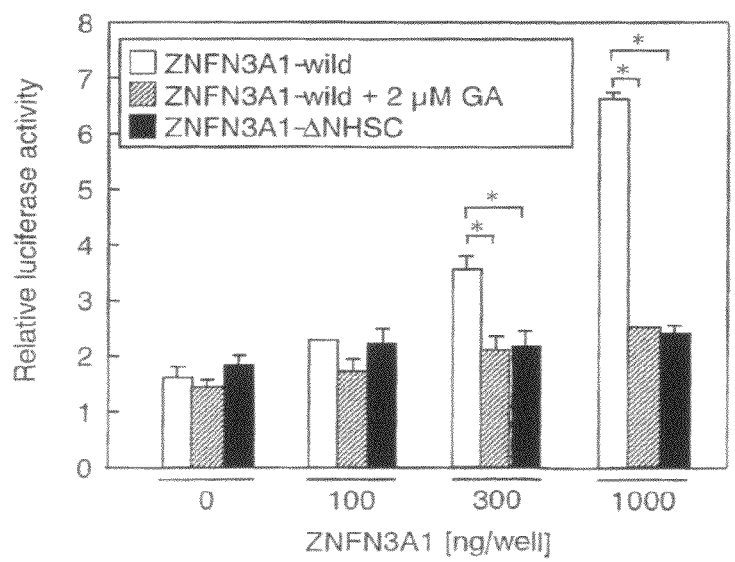

Fig. 8
a
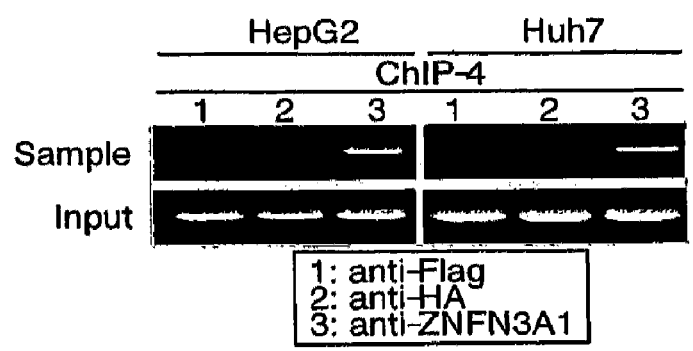
b
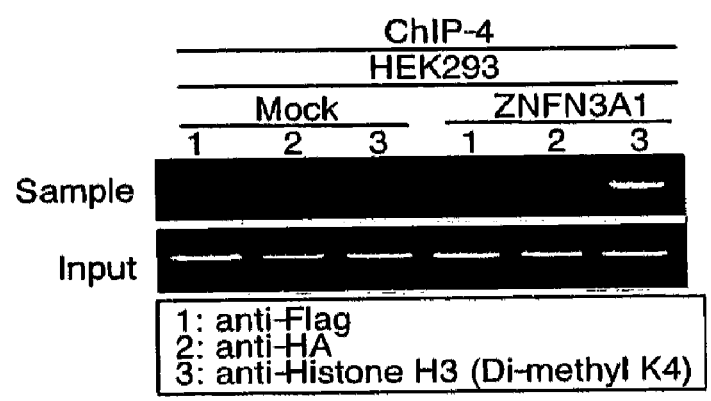

US 8,221,993 B2

METHODS OF DETECTING METHYL TRANSFERASE ACTIVITY AND METHODS OF SCREENING FOR METHYL TRANSFERASE ACTIVITY MODULATORS

This application is a U.S. National Phase Application, filed under 35 U.S.C. §371 of Patent Cooperation Treaty Application Number PCT/JP2005, 001172, filed Jan. 21, 2005 and claims the benefit of U.S. Provisional Application Ser. No. 60/538,658 filed Jan. 23, 2004, the contents of each of the aforementioned applications are hereby incorporated by reference in their entirety.

TECHNICAL FIELD

The present invention relates to transcriptional regulation.

BACKGROUND ART

Hepatocellular carcinoma (HCC) is one of the most common cancers worldwide and its incidence is gradually increasing in Japan as well as in United States (Akriviadis E A, et al., Br J. Surg. 1998 October; 85(10):1319-31). Although recent medical advances have made great progress in diagnosis, a large number of patients with HCCs are still diagnosed at advanced stages and their complete cures from the disease remain difficult. In addition, patients with hepatic cirrhosis or chronic hepatitis have a high risk to HCCs, they may develop multiple liver tumors, or new tumors even after complete removal of initial tumors. Therefore development of highly effective chemotherapeutic drugs and preventive strategies are matters of pressing concern.

Colorectal carcinoma is a leading cause of cancer deaths in developed countries. Specifically, more than 130,000 new cases of colorectal cancer in the United States are reported each year. Colorectal cancer represents about 15% of all cancers. Of these, approximately 5% are directly related to inherited genetic defects. Many patients have a diagnosis of pre-cancerous colon or rectal polyps before the onset of cancer. While many small colorectal polyps are benign, some types may progress to cancer. The most widely used screening test for colorectal cancer is colonoscopy. This method is used to visualize a suspicious growth and/or take a tissue biopsy. Typically, the tissue biopsy is histologically examined and a diagnosis delivered based on the microscopic appearance of the biopsied cells. However, this method is limited in that it yields subjective results and can not be used for very early detection of pre-cancerous states. The development of a sensitive, specific and convenient diagnostic system for detecting very early-stage colorectal cancers or pre-malignant lesions is highly desirable as it could ultimately eliminate this disease.

SUMMARY OF THE INVENTION

The present invention is based in part on the discovery of the methyl transferase activity of ZNFN3A1, a polypeptide which is involved in proliferation of cancer cells. Moreover, the methyl transferase activity of ZNFN3A1 is expressed in the presence of 90-kD heat shock protein (HSP90A).

Accordingly, the invention features a method of measuring methyl transferase activity by contacting a polypeptide of the invention with a methyl transferase substrate and a co-factor under conditions suitable for methylation of the substrate and detecting the methylation level of the substrate. The polypeptide of the invention is a ZNFN3A1 polypeptide or functional equivalent thereof. For example, a polypeptide of the invention may comprise the amino acid sequence of SEQ ID NO: 51. Alternatively, the polypeptides of the invention can include an amino acid sequence of SEQ ID NO: 51 where one or more amino acids are substituted, deleted, or inserted and the polypeptide has a biological activity of the polypeptide of SEQ ID NO:51. Biological activity of the polypeptide of SEQ ID No:51 includes for example the promotion of cell proliferation and the transcriptional activation of target genes. Additionally, the polypeptide includes a 428-amino acid protein encoded by the open reading frame of SEQ ID NO:50 or a polynucleotide that hybridizes under stringent conditions, e.g., low or high, to the nucleotide sequence of SEQ ID NO:50 and has a biological activity of SEQ ID NO:51. A low stringent condition is, for example, 42° C., 2×SSC, 0.1% SDS, or preferably 50° C., 2×SSC, 0.1% SDS. Preferably, a high stringent conditions is used. A high stringent condition is, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors such as temperature and salt concentration can influence the stringency of hybridization and one skilled in the art can suitably select the factors to achieved the requisite stringency. Optionally, the polypeptide is further contacted with 90-kD heat shock protein. Methylation is defined as the catalysis of the transfer of a methyl group to an another compound, e.g., acceptor molecule. Methylation is detected by methods such as using a radioactive methyl donor. The substrate is any compound capable of accepting a methyl group such as a protein, a nucleic acid (RNA or DNA) or a small molecule. For example, the substrate is a histone or a fragment of a histone containing the methylation region. Actually, it is confirmed that histone H3 lysine 4 can be methylated by ZNFN3A1. Therefore, histone H3, or the fragment thereof containing lysine 4, is useful as the substrate. The co-factor, e.g., the methyl donor, is any compound capable of donating a methyl group. For example, the co-factor is S-adenosyl-L-methionine. Suitable conditions for methylation include for example basic buffer conditions know in the art such as Tris-HCl.

The invention further provides methods of identifying an agent that modulates (e.g., increases or decreases) methyl transferase activity by contacting a polypeptide of the invention with a methyl transferase substrate and a co-factor under conditions suitable for methylation of the substrate in the presence of a test agent and determining the methylation level of the substrate. A decrease of the level of methylation compared to a normal control methylation level indicates that the test agent is an inhibitor of methyl transferase activity. Compounds that inhibit (e.g., decreases) methyl transferase activity are useful for treating, preventing or alleviating a symptom of colorectal cancer or hepatocellular carcinoma. For example, the compounds inhibit the proliferation of cancer cells. Alternatively, an increase of the level or activity compared to a normal control level indicates that the test agent is an enhancer of methyl transferase activity. By normal control level is meant a level of methylation of a substrate detected in the absence of the test compound.

The invention provides a method for screening a compound for treating colorectal cancer or hepatocellular carcinoma by contacting a polypeptide with a heat shock protein 90A (HSP90A) polypeptide in the presence of a test agent and detecting binding between the polypeptide and HSP90A. The binding of the polypeptide and HSP90A in the presence of the test compound compared to the absence of the test compound. Test compounds which decrease the binding of the polypeptide and HSP90A are selected. Binding of the polypeptide and HSP90A is defined as a non-covalent association between the polypeptide and HSP90A. Binding is measures by methods known in the art such as a yeast two-hybrid screening system.

The invention also encompasses compositions and methods for alleviating a symptom of a colorectal cancer or hepatocellular carcinoma by contacting a colorectal cancer cell or hepatocellular carcinoma cells with a compound identified as described above. For example, a method of treating a either or both of colorectal cancer and hepatocellular carcinoma is carried out by administering to a mammal, e.g. a human patient having been diagnosed with such a disease state, with a composition containing a pharmaceutically effective amount of the compound identified as described above and a pharmaceutical carrier.

The invention also provides a kit for detecting methyl transferase activity of a compound with a methyl transferase polypeptide, a substrate, a cofactor, and HSP90A. The reagents are packaged together in the form of a kit. The reagents are packaged in separate containers, e.g., a methyl transferase polypeptide of the invention, substrate, co-factor, a control reagent (positive and/or negative), and/or a detectable label. Another embodiment of the invention is a kit for detecting the activity of a test compound to regulate the methyltransferase activity, and/or binding between ZNFN3A1 polypeptide of the invention and heat shock protein 90 A polypeptide (HSP90A). The kit includes ZNFN3A1 polypeptide or fragment thereof and an HSP90A polypeptide. In some aspects of the embodiment ZNFN3A1 is a polypeptide, preferably a recombinant polypeptide, comprising an amino acid sequence having a SET domain of native ZNFN3A1. Furthermore, the invention also provides a kit for screening for a compound for treating colorectal cancer or hepatocellular carcinoma, said kit comprising the components of a polypeptide comprising an contiguous amino acid sequence that selected from the amino acid sequence of SEQ ID NO: 51, and wherein the amino acid sequence comprises either or both of NHSCDPN (SEQ ID NO:52) and GEELTICY (SEQ ID NO:53); and S-adenosyl-L-methionine. Instructions (e.g., written, tape, VCR, CD-ROM, etc.) for carrying out the assay are included in the kit. The assay format of the kit is a transferase assay or binding assay known in the art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

FIG. 1A is an illustration depicting conserved sequences in the SET domains of methyl transferases.

FIG. 1B is a photograph of a SDS-PAGE gel showing the interaction between wild-type ZNFN3A1 and S-adenosyl-L-methionine (SAM). Equal amount of wild-type or mutant ZNFN3A1 (arrowhead) was incubated with [$^3$H]-labeled SAM (top panel). SAM-associated ZNFN3A1 (arrowhead) was detected by fluorogram (bottom panel).

FIG. 1C is a photograph of an in vitro HMTase assay of SET-domain of ZNFN3A1 with/without recombinant HSP90A. SET7 served as a control.

FIG. 2A is a photograph of an in vitro histone H3-K4 methyltransferase assay. Histone H3 was incubated with wild-type or mutant ZNFN3A1, or SET7 in the presence SAM and HSP90A.

FIG. 2B is a photograph showing inhibition of H3-K4 di-methylation by the addition of specific peptides to di-methylated H3-K4.

FIG. 2C is a photograph of an in vitro histone H3-K9 methyltransferase assay. SUV39H1 served as a positive control.

FIG. 4A is a bar chart showing the effect of oncogenic activity of ZNFN3A1 in HEK293 cells. Number of viable cells was measured by Cell Counting Kit-8 at Day 14 after the transfection. *, a significant difference (p<0.05) determined by a Fisher's protected least-significant test.

FIG. 4B is a bar chart showing the effect of oncogenic activity of ZNFN3A1 in HCT116 cells. Number of viable cells was measured by Cell Counting Kit-8 at Day 14 after the transfection. *, a significant difference (p<0.05) determined by a Fisher's protected least-significant test.

FIG. 6A is a photograph of a showing exogeneous expression of ZNFN3A1 in HEK293 cells. Time-dependent expression of ZNFN3A1 in cells transfected with pcDNA (Mock) or pcDNA-ZNFN3A1 was examined by western blot analysis.

FIG. 6B is a photograph of a showing expression of candidate downstream genes in response to exogenous ZNFN3A1. Semi-quantitative RT-PCR analysis was performed using RNA from HEK293 cells transfected with pcDNA-ZNFN3A1 or mock.

FIG. 7A is an illustration depicting the putative ZNFN3A1-binding sequences in the 5'-flanking region of Nkx2.8. The HSP90A-dependent transactivation of Nkx2.8 by ZNFN3A1 express through its interaction with putative binding sequences.

FIG. 7B is a photograph depicting identification of ZNFN3A1-binding elements in the Nkx2.8 promoter region by ChIP assay.

FIG. 7C is a bar chart depicting the results of an in vitro binding assay between recombinant GST-ZNFN3A1 and a double-stranded DNA probe containing the ZNFN3A1-binding element (ZBE).

FIG. 7D are bar charts showing transcriptional assay of Nkx2.8 containing wild-type or mutant ZNFN3A1-binding element (ZBE) in the presence or absence of ZNFN3A1-siRNA in HCC cells.

FIG. 7E is a photograph of a gel showing expression of Nkx2.8 in response to exogeneous expression of wild-type (lane 2 and 3) or mutant (lane 4 and 5) ZNFN3A1 in HEK293 cells. Addition of HSP90A-specific inhibitor, geldanamycin, diminished the enhanced expression of Nkx2.8 caused by wild-type ZNFN3A1 (lane 3).

FIG. 7F is a bar chart showing the effect of wild-type or mutant ZNFN3A1 on the luciferase activity in HEK293-Nkx2.8Luc cells that contain integrated Nkx2.8 promoter-luciferase gene in the genome.

FIG. 8A is a photograph of a showing interaction between endogenous ZNFN3A1 and the ChIP-4 region of Nkx2.8 in hepatoma cells.

FIG. 8B is a photograph of a showing interaction between di-methylated histone H3 lysine 4 (H3-K4) and the ChIP-4 in the presence of ZNFN3A1 in HEK293 cells.

DETAILED DESCRIPTION OF THE INVENTION

Figure 3:
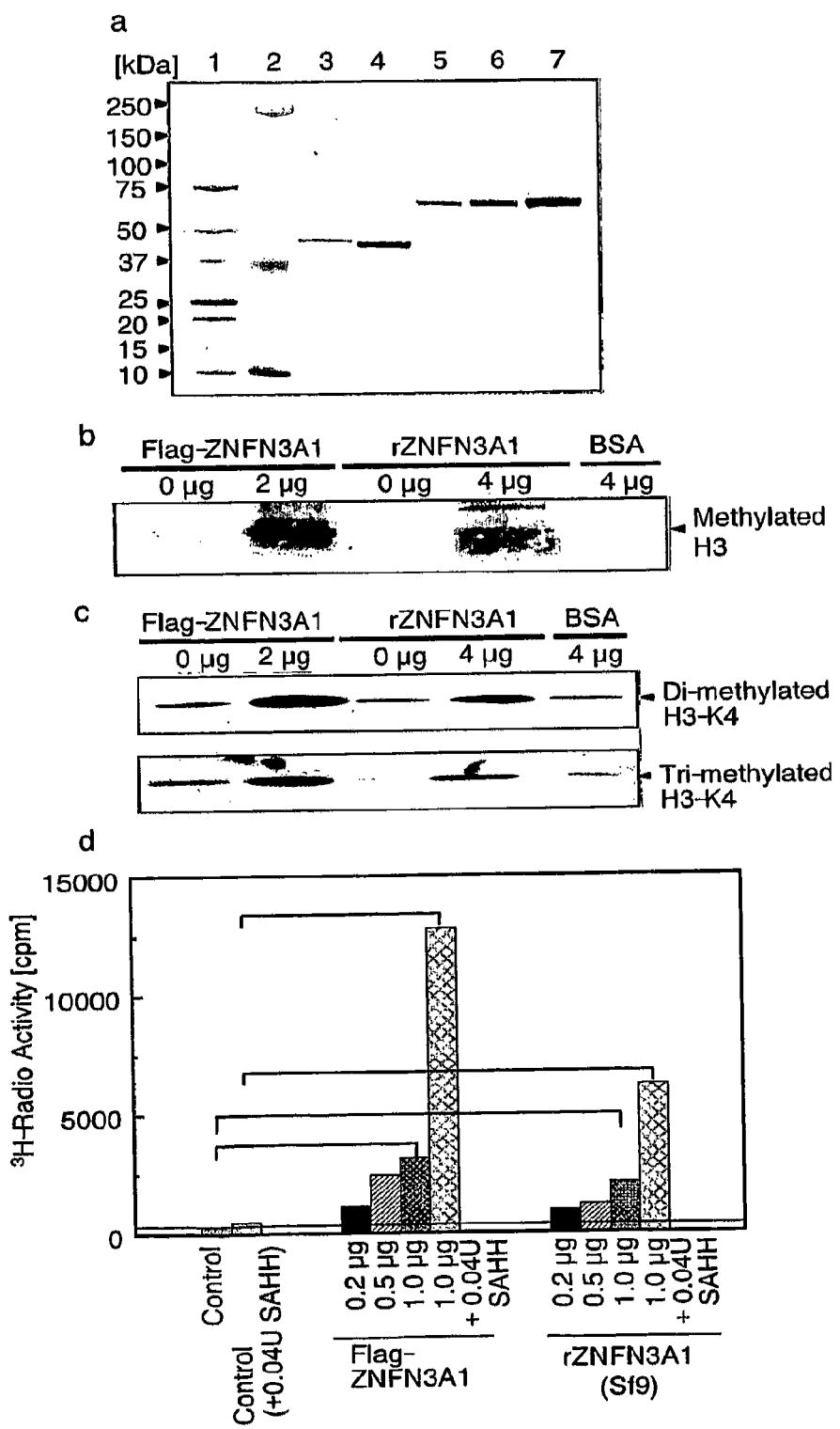
FIG. 3A is a photograph of a SDS-PAGE gel showing the detection of immunoprecipitated and recombinant ZNFN3A1 protein by CBB-staining. Lane 1: protein marker1; Lane 2: protein marker2; Lane 3: immunoprecipitated Flag-tagged ZNFN3A1; Lane 4: recombinant ZNFN3A1 protein; Lane 5: albumin (1 µg); Lane 6: albumin (2 µg); Lane 7: albumin (5 µg).
FIG. 3B is a photograph depicting in vitro histone H3 HMTase activity of immunoprecipitated Flag-ZNFN3A1 and recombinant ZNFN3A1 protein.
FIG. 3C is a photograph depicting di-methylated (upper panel) and tri-methylated (lower panel) histone H3-K4 by immunoprecipitated Flag-ZNFN3A1 or recombinant ZNFN3A1 protein.
FIG. 3D is a bar chart showing the effect of SAHH on the HMTase activity of ZNFN3A1.

The present invention is based in part on the discovery of a novel histone methyl transferase, ZNFN3A1, which is involved in proliferation of cancer cells. The histone methyl transferase activity of ZNFN3A1 is expressed in the presence of 90-kD heat shock protein (HSP90A), thus HSP90A plays a role in for a histone methyl transferase activity.

ZNFN3A1 expression is markedly elevated in colorectal carcinoma and hepatocellular carcinoma (HCCs) compared to non-cancerous liver and colorectal tissues (WO 03/27143). The ZNFN3A1 cDNA consists of 1622 nucleotides that contain an open reading frame of 1284 nucleotides as set forth in SEQ. ID. NO:50. The open reading frame encodes a 428-amino acid protein with a zinc finger motif and a SET domain, as shown in SEQ. ID. NO:51. The subcellular localization of ZNFN3A1 protein is altered during cell cycle progression and by the density of cultured cells. ZNFN3A1 protein accumulates in the nucleus when cells are in middle to late S phase or cultured in sparse conditions. Whereas, ZNFN3A1 protein localizes in the cytoplasm as well as in the nucleus when cells are in other phases of the cell cycle or grown in a dense condition.

ZNFN3A1 contains a SET domain defined by two conserved amino acid sequences, "NHSCXXN" (SEQ ID NO:54) and "GEELXXXY" (SEQ ID NO:55). (FIG. 1A) Genes which encode proteins with a SET domain(s) are classified into four families, namely SUV39, SET1, SET2 and RIZ families according to the homology of their SET domains. The SET domain of ZNFN3A1 does not contain any pre-SET, post-SET, AWS, SANT or C2H2 domains, which are conserved in these subfamilies, thus ZNFN3A1 may constitute a new class of subfamily of SET domain proteins.

ZNFN3A1 directly associates with a RNA helicase KIAA0054, and forms a complex with RNA polymerase II, which activates transcription of downstream genes including epidermal growth factor receptor (EGFR) through a direct binding of the complex with an element of "(C)CCCTCC(T)" in the 5' flanking region of the EGFR gene. Moreover, ZNFN3A1 has been shown to associate with RNA helicase (HELZ) and 90-kD heat shock protein (HSP90A).

Exogenous expression of ZNFN3A1 into NIH3T3 cells resulted in increased cell growth. In contrast, suppression of its expression with antisense S-oligonucleotides resulted in a significant growth-inhibition of hepatoma cells. Furthermore, it was confirmed that siRNA of ZNFN3A1 can also inhibit the proliferation of hepatoma cells and colorectal adenocarcinomas (WO2004/76623). These findings indicate that ZNFN3A1 renders oncogenic activities to cancer cells by transcriptional activation of target genes including EGFR through a complex with RNA helicase and RNA polymerase II, and that inhibition of the activity of the complex is a strategy for the treatment of colorectal carcinoma and hepatocellular carcinoma. Deregulation of other SET domain proteins have been shown to be involved in human neoplasms. For example in human leukemia, frequent translocations are observed in MLL (10,11), the human homolog of *Drosophila trithorax* gene that belongs to SET1 family. Although it is unclear whether loss or gain of MLL function is responsible for the oncogenesis, MLL activates transcription of the Hox gene through H3 lysine 4-specific methylation mediated by methylase activity of the SET domain (12) through its direct binding to the Hox promoter sequences. MLL2 and EZH2, two members of SET1 family are amplified in pancreatic cancers, gliomas, or hormone-refractory, metastatic prostate cancers (13-15).

The invention thus provides a method of screening for a compound that modulates ZNFN3A1 methyltransferase activity. The method is practiced by contacting a ZNFN3A1 polypeptide or functional equivalent thereof having methyl transferase activity with one or more candidate compounds, and assaying methyl transferase activity of the contacted ZNFN3A1 or the functional equivalent. A compound that modulates methyl transferase activity of the ZNFN3A1 or functional equivalent is thereby identified.

In the present invention, the term "functionally equivalent" means that the subject protein has the same or substantially the same methyl transferase activity as ZNFN3A1. In particular, the protein catalyzes the methylation of histone H3 or a fragment of histone H3 comprising lysine 4. Whether a subject protein has the target activity can be determined by the present invention. Namely, the methyl transferase activity can be determined by contacting a polypeptide with a substrate (e.g., histone H3 or fragment comprising lysine 4) and a co-factor (e.g., S-adenosyl-L-methionine) under conditions suitable for methylation of the substrate and detecting the methylation level of the substrate.

Methods for preparing proteins functional equivalent to a given protein are well known by a person skilled in the art and include known methods of introducing mutations into the protein. For example, one skilled in the art can prepare proteins functional equivalent to the human ZNFN3A1 protein by introducing an appropriate mutation in the amino acid sequence of the human ZNFN3A1 protein by site-directed mutagenesis (Hashimoto-Gotoh, T. et al. (1995), Gene 152, 271-275; Zoller, M J, and Smith, M. (1983), Methods Enzymol. 100, 468-500; Kramer, W. et al. (1984), Nucleic Acids Res. 12, 9441-9456; Kramer W, and Fritz H J. (1987) Methods. Enzymol. 154, 350-367; Kunkel, T A (1985), Proc. Natl. Acad. Sci. USA. 82, 488-492; Kunkel (1988), Methods Enzymol. 85, 2763-2766). Amino acid mutations can occur in nature, too. The protein used in the present invention includes those proteins having the amino acid sequences of the human ZNFN3A1 protein in which one or more amino acids are mutated, provided the resulting mutated proteins are functional equivalent to the human ZNFN3A1 protein. The number of amino acids to be mutated in such a mutant is generally 10 amino acids or less, preferably 6 amino acids or less, and more preferably 3 amino acids or less. The SET-domain "NHSCXXN" (SEQ ID NO:54) and "GEELXXXY" (SEQ ID NO:55) may be conserved in the amino acid sequence of the mutated proteins for maintain the methyl transferase activity ("X" indicates any amino acid).

Mutated or modified proteins, proteins having amino acid sequences modified by deleting, adding and/or replacing one or more amino acid residues of a certain amino acid sequence, have been known to retain the original biological activity (Mark, D. F. et al., Proc. Natl. Acad. Sci. USA (1984) 81, 5662-5666, Zoller, M. J. & Smith, M., Nucleic Acids Research (1982) 10, 6487-6500, Wang, A. et al., Science 224, 1431-1433, Dalbadie-McFarland, G. et al., Proc. Natl. Acad. Sci. USA (1982) 79, 6409-6413).

The amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a protein to which one or more amino acids residues are added to the amino acid sequence of human ZNFN3A1 protein (SEQ ID NO: 51) is a fusion protein containing the human ZNFN3A1 protein. Fusion proteins are, fusions of the human ZNFN3A1 protein and other peptides or proteins, and are used in the present invention. Fusion proteins can be made by techniques well known to a person skilled in the art, such as by linking the DNA encoding the human ZNFN3A1 protein of the invention with DNA encoding other peptides or proteins, so that the frames match, inserting the fusion DNA into an expression vector and expressing it in a host. There is no restriction as to the peptides or proteins fused to the protein of the present invention.

Known peptides that can be used as peptides that are fused to the ZNFN3A1 protein include, for example, FLAG (Hopp, T. P. et al., Biotechnology (1988) 6, 1204-1210), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Examples of proteins that may be fused to a protein of the invention include GST (glutathione-S-transferase), Influenza agglutinin (HA), immunoglobulin constant region, galactosidase, MBP (maltose-binding protein), and such.

Fusion proteins can be prepared by fusing commercially available DNA, encoding the fusion peptides or proteins discussed above, with the DNA encoding the protein of the present invention and expressing the fused DNA prepared.

An alternative method known in the art to isolate functional equivalent proteins is, for example, the method using a hybridization technique (Sambrook, J. et al., Molecular Cloning 2nd ed. 9.47-9.58, Cold Spring Harbor Lab. Press, 1989). One skilled in the art can readily isolate a DNA having high homology with a whole or part of the ZNFN3A1 DNA sequence (e.g., SEQ ID NO: 50) encoding the human ZNFN3A1 protein, and isolate functional equivalent proteins to the human ZNFN3A1 protein from the isolated DNA. The proteins used for the present invention include those that are encoded by DNA that hybridize with a whole or part of the DNA sequence encoding the human ZNFN3A1 protein and are functional equivalent to the human ZNFN3A1 protein. These proteins include mammal homologues corresponding to the protein derived from human or mouse (for example, a protein encoded by a monkey, rat, rabbit and bovine gene). In isolating a cDNA highly homologous to the DNA encoding the human ZNFN3A1 protein from animals, it is particularly preferable to use tissues from skeletal muscle, testis, HCC, or colorectal tumors.

The condition of hybridization for isolating a DNA encoding a protein functional equivalent to the human ZNFN3A1 protein can be routinely selected by a person skilled in the art. For example, hybridization may be performed by conducting prehybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringent condition is, for example, 42° C., 2×SSC, 0.1% SDS, or preferably 50° C., 2×SSC, 0.1% SDS. More preferably, high stringent condition is used. A high stringent condition is, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors such as temperature and salt concentration can influence the stringency of hybridization and one skilled in the art can suitably select the factors to achieved the requisite stringency.

In place of hybridization, a gene amplification method, for example, the polymerase chain reaction (PCR) method, can be utilized to isolate a DNA encoding a protein functional equivalent to the human ZNFN3A1 protein, using a primer synthesized based on the sequence information of the DNA (SEQ ID NO: 50) encoding the human ZNFN3A1 protein (SEQ ID NO: 51).

Proteins that are functional equivalent to the human ZNFN3A1 protein encoded by the DNA isolated through the above hybridization techniques or gene amplification techniques, normally have a high homology to the amino acid sequence of the human ZNFN3A1 protein. "High homology" (also referred to as "high identity") typically refers to the degree of identity between two optimally aligned sequences (either polypeptide or polynucleotide sequences). Typically, high homology or identity refers to homology of 40% or higher, preferably 60% or higher, more preferably 80% or higher, even more preferably 85%, 90%, 95%, 98%, 99%, or higher. The degree of homology or identity between two polypeptide or polynucleotide sequences can be determined by following the algorithm in "Wilbur, W. J. and Lipman, D. J. Proc. Natl. Acad. Sci. USA (1983) 80, 726-730".

A protein useful in the context of the present invention may have variations in amino acid sequence, molecular weight, isoelectric point, the presence or absence of sugar chains, or form, depending on the cell or host used to produce it or the purification method utilized. Nevertheless, so long as it has a function equivalent to that of a human ZNFN3A1 protein (SEQ ID NO: 51), it is useful in the present invention.

The proteins useful in the context of the present invention can be prepared as recombinant proteins or natural proteins, by methods well known to those skilled in the art. A recombinant protein can be prepared by inserting a DNA, which encodes the protein of the present invention (for example, the DNA comprising the nucleotide sequence of SEQ ID NO: 50), into an appropriate expression vector, introducing the vector into an appropriate host cell, obtaining the extract, and purifying the protein by subjecting the extract to chromatography, for example, ion exchange chromatography, reverse phase chromatography, gel filtration, or affinity chromatography utilizing a column to which antibodies against the protein of the present invention is fixed, or by combining more than one of aforementioned columns.

Also when the protein useful in the context of the present invention is expressed within host cells (for example, animal cells and *E. coli*) as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions other than the objective protein by cutting with thrombin or factor-Xa as required.

A natural protein can be isolated by methods known to a person skilled in the art, for example, by contacting the affinity column, in which antibodies binding to the ZNFN3A1 protein described below are bound, with the extract of tissues or cells expressing the protein of the present invention. The antibodies can be polyclonal antibodies or monoclonal antibodies.

In the present invention, methyl transferase activity of a ZNFN3A1 polypeptide can be determined by methods known in the art. For example, the ZNFN3A1 and a substrate can be incubated with a labeled methyl donor, under suitable assay conditions. A histone H3, histone H3 peptide, and S-adenosyl-[methyl-$^{14}$C]-L-methionine, or S-adenosyl-[methyl-$^{3}$H]-L-methionine preferably can be used as the substrate and methyl donor, respectively. Transfer of the radiolabel to the histone or histone peptide can be detected, for example, by SDS-PAGE electrophoresis and fluorography. Alternatively, following the reaction the histone or histone peptides can be separated from the methyl donor by filtration, and the amount of radiolabel retained on the filter quantitated by scintillation counting. Other suitable labels that can be attached to methyl donors, such as chromogenic and fluorescent labels, and methods of detecting transfer of these labels to histones and histone peptides, are known in the art.

Alternatively, methyl transferase activity of ZNFN3A1 can be determined using an unlabeled methyl donor (e.g. S-adenosyl-L-methionine) and reagents that selectively recognize methylated histones or histone peptides. For example, after incubation of the ZNFN3A1, substrate to be methylated and methyl donor, under the condition capable of methylation of the substrate, methylated substrate can be detected by immunological method. Any immunological techniques using an antibody recognizing methylated substrate can be used for the detection. For example, an antibody against methylated histone is commercial available (abcam Ltd.). ELISA or Immunoblotting with antibodies recognizing methylated histone can be used for the present invention.

Instead of using antibodies, methylated histones can be detected using reagents that selectively bind methylated histones with high affinity. Such reagents are known in the art or can be determined by screening assays known in the art. An exemplary binding reagent is heterochromatin protein HP1, which binds histone H3 when methylated at lysine 4 (H3-K4). HP1, or a binding fragment thereof, can be labeled, and the HP1 or fragment bound to methylated H3-K4 detected. Alternatively, the HP1 or fragment need not be labeled, and can instead be detected using an anti-HP1 antibody in an ELISA assay.

In the present invention, an agent enhancing the methylation of the substance can be used. For example, H3 methyltransferase activity of Flag-tagged ZNFN3A1 was significantly higher in the presence of S-adenosyl homocysteine hydrolase (SAHH) than the absence of SAHH (FIG. 3d).

Thus, SAHH or functional equivalent thereof are preferable enhancing agent for the methylation. The agent enhances the methylation of the substance, the methyltransferase activity can be determined with higher sensitivity thereby. ZNFN3A1 may be contacted with substrate and cofactor under the existence of the enhancing agent.

Various low-throughput and high-throughput enzyme assay formats are known in the art and can be readily adapted for detection or measuring of methyl transferase activity of ZNFN3A1. For high-throughput assays, the histone or histone peptide substrate can conveniently be immobilized on a solid support, such as a multiwell plate, slide or chip. Following the reaction, the methylated product can be detected on the solid support by the methods described above. Alternatively, the methyl transferase reaction can take place in solution, after which the histone or histone peptide can be immobilized on a solid support, and the methylated product detected. To facilitate such assays, the solid support can be coated with streptavidin and the histone labeled with biotin, or the solid support can be coated with anti-histone antibodies. The skilled person can determine suitable assay formats depending on the desired throughput capacity of the screen.

ZNFN3A1 or the functional equivalent requires heat shock protein 90A (HSP90A) for expressing the methyl transferase activity. Therefore, a compound that interferes binding between ZNFN3A1 or the functional equivalent and HSP90A is useful for modulation of the methyl transferase activity. The compound can be screened through the following method. Thus, the present invention also provides a method of screening for a compound for treating colorectal cancer or hepatocellular carcinoma, said method comprising the steps of:

a. contacting a polypeptide selected from the group consisting of:
    i. a polypeptide comprising the amino acid sequence of SEQ ID NO: 51;
    ii. a polypeptide comprising the amino acid sequence of SEQ ID NO: 51 wherein one or more amino acids are substituted, deleted, or inserted and said polypeptide has a biological activity equivalent to the polypeptide consisting of the amino acid sequence of SEQ ID NO: 51;
    iii. a polypeptide that comprises the amino acid sequence having at least about 80% homology to SEQ ID NO: 51; and
    iv. a polypeptide encoded by a polynucleotide that hybridizes under stringent conditions to a polynucleotide consisting of the nucleotide sequence of SEQ ID NO: 50, wherein the polypeptide has a biological activity equivalent to a polypeptide consisting of the amino acid sequence of SEQ ID NO: 51; with a heat shock protein 90A polypeptide (HSP90A) in the presence of a test compound;
  b. detecting binding between the polypeptide and HSP90A;
  c. comparing the binding of the polypeptide and HSP90A in the presence of the test compound with that in the absence of the test compound, and
  d. selecting a test compound which decreases the binding of the polypeptide and HSP90A.

In the present invention, the binding of the polypeptide and HSP90A can be detected via any suitable method known to those of skill in the art. For example, either of the polypeptide and HSP90A can be bound to solid support, and the other can be labeled with labeling substances for detection. Labeling substances such as radioisotope (e.g., $^{3}$H, $^{14}$C, $^{32}$P, $^{33}$P, $^{35}$S, $^{125}$I, $^{131}$I), enzymes (e.g., alkaline phosphatase, horseradish peroxidase, β-galactosidase, β-glucosidase), fluorescent substances (e.g., fluorescein isothiocyanate (FITC), rhodamine), and biotin/avidin, may be used for the labeling of a polypeptide or HSP90A in the present method. Methods for detection of the labeling substances are well known.

The present invention also encompasses the use of partial peptides of a protein of the present invention. A partial peptide has an amino acid sequence specific to the protein of the ZNFN3A1 and consists of less than about 400 amino acids, usually less than about 200 and often less than about 100 amino acids, and at least about 7 amino acids, preferably about 8 amino acids or more, and more preferably about 9 amino acids or more. The partial peptide can be used, for example, for the screening for a compound that binds to the protein of the ZNFN3A1, and screening for inhibitors of the binding between ZNFN3A1 and co-factor thereof such as SAM. The partial peptide containing the SET-domain preferably used for these screening.

A partial peptide used for the invention can be produced by genetic engineering, by known methods of peptide synthesis, or by digesting the protein of the invention with an appropriate peptidase. For peptide synthesis, for example, solid phase synthesis or liquid phase synthesis may be used.

Figure 5:
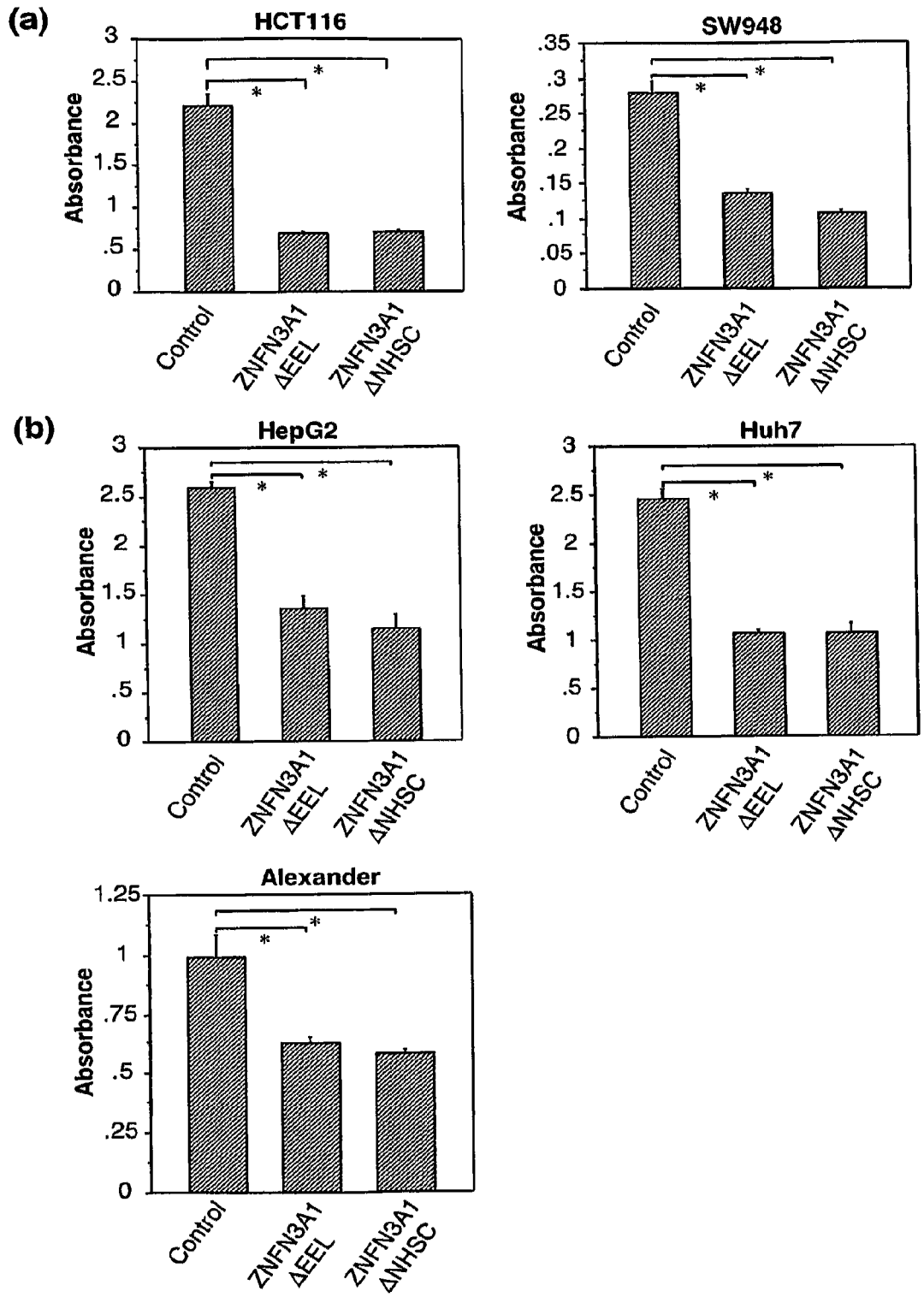
FIG. 5A is a bar chart showing the cell viability of colon cancer lines were measured by Cell Counting Kit-8 14 days after transfection of plasmids. Cells were selected with 0.5 µg/µl G418-containing McCoy's medium for HCT1 16, 1.0 G418-containing L-15 medium for SW948. *, a significant difference (p<0.05) determined by a Fisher's protected least-significant test.
FIG. 5B is a bar chart showing the cell viability of hepatoma cell lines were measured by Cell Counting Kit-8 14 days after transfection of plasmids. Cells were selected with 1.0 µg/µl G418-containing DMEM for HepG2, 0.8 µg/µl G418-containing DMEM for Huh7 and Alexander. *, a significant difference (p<0.05) determined by a Fisher's protected least-significant test.

The ZNFN3A1 mutant having the mutation of SET-domain shows inhibitory effect for the cell proliferation (FIG. 4 or 5). Therefore, the partial peptide of ZNFN3A1 preferably includes the SET-domain "NHSCXXN" (SEQ ID NO:54) and/or "GEELXXXY" (SEQ ID NO:55).

In a further embodiment of the method for screening a compound for treating or preventing HCC or colorectal cancer of the present invention, the method utilizes the binding ability of ZNFN3A1 to co-factor thereof, such as SAM. The proteins having a mutation in the SET-domain which binds to S-adenosyl-L-methionine inhibits the cell proliferation of cancer. These findings suggest that the ZNFN3A1 exerts the function of cell proliferation via its binding to molecules, such as S-adenosyl-L-methionine. Thus, the inhibition of the binding between the ZNFN3A1 and the co-factor thereof leads to the suppression of cell proliferation, and compounds inhibiting the binding serve as pharmaceuticals for treating or preventing a HCC or colorectal cancer.

This screening method includes the steps of:
  a. contacting a polypeptide comprising an a contiguous amino acid sequence from the amino acid sequence of SEQ ID NO: 51, and wherein the amino acid sequence comprises either or both of NHSCDPN (SEQ ID NO:52) and GEELTICY (SEQ ID NO:53), with an S-adenosyl-L-methionine in the presence of a test compound;
  b. detecting binding between the polypeptide and S-adenosyl-L-methionine;
  c. comparing the binding of the polypeptide and S-adenosyl-L-methionine in the presence of the test compound with that in the absence of the test compound, and
  d. selecting a test compound which decreases the binding of the polypeptide and S-adenosyl-L-methionine.

The polypeptide to be used for the screening may be a recombinant polypeptide or a protein derived from the nature, or may also be a partial peptide thereof so long as it retains the binding ability to S-adenosyl-L-methionine. The polypeptide to be used in the screening can be, for example, a purified polypeptide, a soluble protein, a form bound to a carrier, or a fusion protein fused with other polypeptides.

Any test compound, for example, cell extracts, cell culture supernatant, products of fermenting microorganism, extracts from marine organism, plant extracts, purified or crude proteins, peptides, non-peptide compounds, synthetic micromolecular compounds and natural compounds, can be used.

Test compounds useful in the assays described herein can also be antibodies that specifically bind ZNFN3A1 or partial ZNFN3A1 peptides that lack methyl transferase activity. For example, antibodies (e.g., monoclonal antibodies) can be tested for the ability to block the binding between ZNFN3A1 and its substrate, S-adenosyl-L-methionine or HSP90A. Similarly partial ZNFN3A1' peptides can be tested for the ability to inhibit the binding between ZNFN3A1 and its substrate, S-adenosyl-L-methionine or HSP90A can be used as inhibitors of ZNFN3A1 activity. Such antibodies and partial peptides can thus be used as inhibitors of ZNFN3A1 activity.

As a method of screening for compounds that inhibit the binding between the ZNFN3A1 and S-adenosyl-L-methionine, many methods well known by one skilled in the art can be used. Such a screening can be carried out as an in vitro assay system, for example, in acellular system. More specifically, first, either the polypeptide, or S-adenosyl-L-methionine is bound to a support, and the other member is added together with a test sample thereto. Next, the mixture is incubated, washed, and the other member bound to the support is detected and/or measured.

Examples of supports that may be used for binding proteins include insoluble polysaccharides, such as agarose, cellulose, and dextran; and synthetic resins, such as polyacrylamide, polystyrene, and silicon; preferably commercial available beads and plates (e.g., multi-well plates, biosensor chip, etc.) prepared from the above materials may be used. When using beads, they may be filled into a column.

The binding of a polypeptide or S-adenosyl-L-methionine to a support may be conducted according to routine methods, such as chemical bonding, and physical adsorption. Alternatively, a polypeptide may be bound to a support via antibodies specifically recognizing the polypeptide. Moreover, binding of a polypeptide to a support can be also conducted by means of avidin and biotin binding.

The binding between polypeptide and S-adenosyl-L-methionine is carried out in buffer, for example, but are not limited to, phosphate buffer and Tris buffer, as long as the buffer does not inhibit the binding between the proteins.

In the present invention, a biosensor using the surface plasmon resonance phenomenon may be used as a mean for detecting or quantifying the binding the polypeptide and S-adenosyl-L-methionine. When such a biosensor is used, the interaction between the polypeptide and S-adenosyl-L-methionine can be observed real-time as a surface plasmon resonance signal, using only a minute amount of polypeptide and without labeling (for example, BIAcore, Pharmacia). Therefore, it is possible to evaluate the binding between the polypeptide and polypeptide and S-adenosyl-L-methionine using a biosensor such as BIAcore.

Alternatively, either the polypeptide or polypeptide and S-adenosyl-L-methionine, may be labeled, and the label may be used to detect or measure the bound polypeptide or polypeptide and S-adenosyl-L-methionine. Specifically, after pre-labeling one of the polypeptide or S-adenosyl-L-methionine, the labeled member is contacted with the other member in the presence of a test compound, and then, bound member are detected or measured according to the label after washing.

Labeling substances such as radioisotope (e.g., $^{3}$H, $^{14}$C, $^{32}$P, $^{33}$P, $^{35}$S, $^{125}$I, $^{131}$I), enzymes (e.g., alkaline phosphatase, horseradish peroxidase, β-galactosidase, β-glucosidase), fluorescent substances (e.g., fluorescein isothiocyanate (FITC), rhodamine), and biotin/avidin, may be used for the labeling of a polypeptide or S-adenosyl-L-methionine in the present method. When the polypeptide or S-adenosyl-L-methionine is labeled with radioisotope, the detection or measurement can be carried out by liquid scintillation. Alternatively, polypeptide or S-adenosyl-L-methionine labeled with enzymes can be detected or measured by adding a substrate of the enzyme to detect the enzymatic change of the substrate, such as generation of color, with absorptiometer. Further, in case where a fluorescent substance is used as the label, the bound member may be detected or measured using fluorophotometer.

Furthermore, the binding of the polypeptide and S-adenosyl-L-methionine can be also detected or measured using antibodies to the polypeptide. For example, after contacting the S-adenosyl-L-methionine immobilized on a support with a test compound and the polypeptide, the mixture is incubated and washed, and detection or measurement can be conducted using an antibody against the polypeptide.

In case of using an antibody in the present screening, the antibody is preferably labeled with one of the labeling substances mentioned above, and detected or measured based on the labeling substance. Furthermore, the antibody bound to the protein in the screening of the present invention may be detected or measured using protein G or protein A column.

The compound isolated by the screening is a candidate for drugs that inhibit the methyl transferase activity of ZNFN3A1 and can be applied to the treatment or prevention of HCC or colorectal cancer.

Moreover, compounds in which a part of the structure of the compound inhibiting the methyl transferase activity of ZNFN3A1 is converted by addition, deletion and/or replacement are also included in the compounds obtainable by the screening method of the present invention.

As noted above, the compounds that inhibit the methyl transferase activity of ZNFN3A1 can be either partial peptides that lack the methyl transferase activity of ZNFN3A1 or can be antibodies against ZNFN3A1. As used herein, the term "antibody" refers to an immunoglobulin molecule having a specific structure, that interacts (i.e., binds) only with the antigen that was used for synthesizing the antibody or with an antigen closely related thereto. Furthermore, an antibody may be a fragment of an antibody or a modified antibody, so long as it binds to the proteins encoded by ZNFN3A1 gene. For instance, the antibody fragment may be Fab, F(ab')$_2$, Fv, or single chain Fv (scFv), in which Fv fragments from H and L chains are ligated by an appropriate linker (Huston J. S. et al. Proc. Natl. Acad. Sci. U.S.A. 85:5879-5883 (1988)). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co M. S. et al. J. Immunol. 152:2968-2976 (1994); Better M. and Horwitz A. H. Methods Enzymol. 178:476-496 (1989); Pluckthun A. and Skerra A. Methods Enzymol. 178:497-515 (1989); Lamoyi E. Methods Enzymol. 121:652-663 (1986); Rousseaux J. et al. Methods Enzymol. 121:663-669 (1986); Bird R. E. and Walker B. W. Trends Biotechnol. 9:132-137 (1991)).

An antibody may be modified by conjugation with a variety of molecules, such as polyethylene glycol (PEG). The present invention provides such modified antibodies. The modified antibody can be obtained by chemically modifying an antibody. Such modification methods are conventional in the field. Alternatively, an antibody may comprise as a chimeric antibody having a variable region derived from a nonhuman antibody and a constant region derived from a human antibody, or a humanized antibody, comprising a complementarity determining region (CDR) derived from a nonhuman antibody, the frame work region (FR) derived from a human antibody and the constant region. Such antibodies can be prepared by using known technologies. Humanization can be performed by substituting rodent CDRs or CDR sequences for the corresponding sequences of a human antibody (see e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies comprising human variable regions in addition to human framework and constant regions can also be used. Such antibodies can be produced using various techniques known in the art. For example in vitro methods involve use of recombinant libraries of human antibody fragments displayed on bacteriophage (e.g., Hoogenboom & Winter, J. Mol. Biol. 227:381 (1991), Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

When administrating the compound isolated by the method of the invention as a pharmaceutical for humans and other mammals, such as mice, rats, guinea-pigs, rabbits, cats, dogs, sheep, pigs, cattle, monkeys, baboons, and chimpanzees, the isolated compound can be directly administered or can be formulated into a dosage form using known pharmaceutical preparation methods. For example, according to the need, the drugs can be taken orally, as sugar-coated tablets, capsules, elixirs and microcapsules, or non-orally, in the form of injections of sterile solutions or suspensions with water or any other pharmaceutically acceptable liquid. For example, the compounds can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; and flavoring agents such as peppermint, Gaultheria adenothrix oil and cherry. When the unit-dose form is a capsule, a liquid carrier, such as an oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannnose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80™ and HCO-50.

Sesame oil or Soy-bean oil can be used as a oleaginous liquid and may be used in conjunction with benzyl benzoate or benzyl alcohol as a solubilizer and may be formulated with a buffer, such as phosphate buffer and sodium acetate buffer; a pain-killer, such as procaine hydrochloride; a stabilizer, such as benzyl alcohol and phenol; and an anti-oxidant. The prepared injection may be filled into a suitable ampule.

Methods well known to one skilled in the art may be used to administer the pharmaceutical composition of the present invention to patients, for example as intraarterial, intravenous, or percutaneous injections and also as intranasal, transbronchial, intramuscular or oral administrations. The dosage and method of administration vary according to the body-weight and age of a patient and the administration method; however, one skilled in the art can routinely select a suitable method of administration. If said compound is encodable by a DNA, the DNA can be inserted into a vector for gene therapy and the vector administered to a patient to perform the therapy. The dosage and method of administration vary according to the body-weight, age, and symptoms of the patient but one skilled in the art can suitably select them.

For example, although the dose of a compound that binds to the ZNFN3A1 and regulates its activity depends on the symptoms, the dose is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

The present invention further provides a method for treating a HCC or colorectal cancer in a subject. Administration can be prophylactic or therapeutic to a subject at risk of (or susceptible to) a disorder or having a disorder associated with aberrant the methyl transferase activity of ZNFN3A1. The method includes decreasing the function of ZNFN3A1 in a HCC or colorectal cancer cell. Function can be inhibited through the administration of a compound obtained by the screening method of the present invention.

In another aspect the invention includes pharmaceutical, or therapeutic, compositions containing one or more therapeutic compounds described herein. Alternatively, the present invention also provides use of one or more therapeutic compounds described herein for manufacturing a pharmaceutical, or therapeutic, compositions for treating and/or preventing of HCC or colorectal cancer. Pharmaceutical formulations may include those suitable for oral, rectal, nasal, topical (including buccal and sub-lingual), vaginal or parenteral (including intramuscular, sub-cutaneous and intravenous) administration, or for administration by inhalation or insufflation. The formulations may, where appropriate, be conveniently presented in discrete dosage units and may be prepared by any of the methods well known in the art of pharmacy. All such pharmacy methods include the steps of bringing into association the active compound with liquid carriers or finely divided solid carriers or both as needed and then, if necessary, shaping the product into the desired formulation.

Pharmaceutical formulations suitable for oral administration may conveniently be presented as discrete units, such as capsules, cachets or tablets, each containing a predetermined amount of the active ingredient; as a powder or granules; or as a solution, a suspension or as an emulsion. The active ingredient may also be presented as a bolus electuary or paste, and be in a pure form, i.e., without a carrier. Tablets and capsules for oral administration may contain conventional excipients such as binding agents, fillers, lubricants, disintegrant or wetting agents. A tablet may be made by compression or molding, optionally with one or more formulational ingredients.

Compressed tablets may be prepared by compressing in a suitable machine the active ingredients in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The tablets may optionally be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration may be presented as a suppository with the usual carriers such as cocoa butter or polyethylene glycol. Formulations for topical administration in the mouth, for example buccally or sublingually, include lozenges, comprising the active ingredient in a flavored base such as sucrose and acacia or tragacanth, and pastilles comprising the active ingredient in a base such as gelatin and glycerin or sucrose and acacia. For intra-nasal administration the compounds obtained by the invention may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

For administration by inhalation the compounds are conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflators.

When desired, the above described formulations, adapted to give sustained release of the active ingredient, may be employed. The pharmaceutical compositions may also contain other active ingredients such as antimicrobial agents, immunosuppressants or preservatives.

It should be understood that in addition to the ingredients particularly mentioned above, the formulations of this invention may include other agents conventional in the art having regard to the type of formulation in question, for example, those suitable for oral administration may include flavoring agents.

Preferred unit dosage formulations are those containing an effective dose, as recited below, or an appropriate fraction thereof, of the active ingredient.

For each of the aforementioned conditions, the compositions may be administered orally or via injection at a dose of from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The pharmaceutical composition preferably is administered orally or by injection (intravenous or subcutaneous), and the precise amount administered to a subject will be the responsibility of the attendant physician. However, the dose employed will depend upon a number of factors, including the age and sex of the subject, the precise disorder being treated, and its severity. Also the route of administration may vary depending upon the condition and its severity.

EXAMPLE 1

General Methods

In Vitro Histone Methyl Transferase (HMTase) Assay.

293T cells were transfected with plasmid expressing Flag-tagged ZNFN3A1 (pFLAG-CMV-ZNFN3A1), SET7 protein or mock, and purified tagged proteins by immunoprecipitation with anti-Flag antibody. In vitro HMTase assay was performed according to the protocol (1) with a slight modification. Briefly, immunoprecipitated protein was incubated with 25 μg of free histones (mixture of H3, H2B, H2A and H4; Roche) as substrates and 2.5 μCi S-adenosyl-L-[methyl-$^3$H] methionine as methyl donor in a mixture of 40 μl of methylase activity buffer (50 mM Tris-HCl pH 8.5, 20 mM KCl, 10 mM MgCl$_2$, 10 mM β-mercaptoethanol, 250 mM sucrose), for 60 min at 37° C. For the measurement of histone H3 methyltransferase activity, immunoprecipitated protein was incubated with 1 μg of recombinant histone H3 protein (Upstate) as substrates and 2 μCi S-adenosyl-L-[methyl-$^3$H] methionine (SAM) (Amersham Biosciences) as methyl donor in a mixture of 20 μl of methylase activity buffer (50 mM Tris-HCl pH 8.5, 100 mM NaCl, 10 mM DTT), for 1 hr at 30° C. Proteins were separated by 18% SDS-PAGE and visualized by Coomassie staining and fluorography.

In Vitro Histone H3 Methyltransferase (HMTase) Assay.

H3-K4 specific methyltransferase activity was examined by western blot analysis of recombinant Xenopus H3 protein (UBI) incubated with the immunoprecipitants in the presence of 20 μM unlabeled S-adenosyl-L-methionine (SAM) and 2 μg of HSP90A for 1 hr at 30° C., using antibodies against mono-methylated (Abcam; ab8895), di-methylated (Abcam; ab7766), tri-methylated (Abcam; ab8580) H3-K4, total H3 (Abcam; ab1791), or tri-methylated H3-K9 (UBI; 07523). Lysates of cells transfected with plasmid expressing Flag-tagged wild-type ZNFN3A1, mutant ZNFN3A1, SET7/9, SUV39H1, or mock were immunoprecipitated with anti-Flag antibody (Sigma). Peptides to di-methylated H3-K4 (Abcam; ab7768, ARTK-Me2-QTAR-GGC) and di-methylated H3-K9 (Abcam; ab1772, QTARK-Me2-ST-GGC) were used for competition assay. Recombinant ZNFN3A1 was expressed in E. coli bacteria with plasmids expressing GST-fused ZNFN3A1 or in Sf9 cells with plasmids expressing HA-tagged ZNFN3A1. H3-methyltransferase activity was also analyzed in the presence or absence of 0.04 U SAHH (Sigma) using immunoprecipitated ZNFN3A1 protein or recombinant ZNFN3A1 purified from Sf9 cells.

Colony-Formation Assay

The entire coding sequences of wild-type ZNFN3A1 and mutant ZNFN3A1 (ΔEEL and ΔNHSC) were cloned into the appropriate cloning sites of p3xFLAG-CMV-10 (SIGMA). Plasmids designed to express the sense strand of wild-type ZNFN3A1 (p3xFLAG-CMV-ZNFN3A1) or mutant ZNFN3A1 (p3xFLAG-CMV-ZNFN3A1-ΔEEL, p3xFLAG-CMV-ZNFN3A1-ΔNHSC), or control plasmid (p3xFLAG-CMV-10), were transfected into HEK293, colorectal cancer or hepatoma cells using FuGENE6 reagent according to the supplier's recommendations (Roche). Transfected cells were maintained in culture media supplemented with an optimized concentration of geneticin. Cell viability was measured by Cell Counting Kit-8 according to the manufacturer's protocol (DOJINDO).

Identification of Downstream Genes by cDNA Microarray.

HEK293 cells expressing no ZNFN3A1 were transfected with either pcDNA-ZNFN3A1 or mock vector. RNA was extracted at 18 h after transfection, labeled with Cy3 or Cy5 dye, and subjected to co-hybridization onto in-house cDNA microarray slides containing 13,824 genes as described previously (2, 3). After normalization of the data, genes with signals higher than the cut-off value were further analyzed.

Chromatin Immunoprecipitation (ChIP) Assays.

HEK293, HepG2 and Huh7 cells were transfected with pFLAG-CMV-ZNFN3A1 and then fixed in 1% formaldehyde. The fixed chromatin samples were subjected to immunoprecipitation using ChIP assay kit according to the manufacturer's instructions (Promega). DNA from the HEK293 cells was precipitated with anti-Flag antibody or anti-di-methylated histone H3 antibody, DNA from HepG2 or Huh7 cells with anti-ZNFN3A1 antibody. The sets of primers used for ChIP assay were shown in Table 1.

TABLE 1

Primers used for ChIP assay

| | | | SEQ ID No; |
|---|---|---|---|
| Nkx2.8 ChIP-1; | F: | 5'-TGCATTATTCCGGACTGAACAAATGC-3' | 25 |
| | R: | 5'-GTTGCTAAATTGTAGCGAAGGGCTC-3' | 26 |
| ChIP-2; | F: | 5'-ACCCAAGTACAGAGCCCTTCGCTAC-3' | 27 |
| | R: | 5'-TCACTGCCTGGGCTTTGGTCTTTG-3' | 28 |
| ChIP-3; | F: | 5'-GACCAAAGCCCAGGCAGTGAGAGTG-3' | 29 |
| | R: | 5'-CTGAGGAAGGGCTGGGACAACATTC-3' | 30 |
| ChIP-4; | F: | 5'-TGGCTACAAGCCTCTTCTGTTTTGC-3' | 31 |
| | R: | 5'-AGGGGTGGGTTTATTAGCACCCAGG-3' | 32 |

Luciferase Assay.

The fragment of Nkx2.8 promoter were amplified by PCR using a set of primer, 5'-AGCGGGCCTGGTAC-CAAATTTGTG-3' (SEQ ID NO; 46) and 5'-CCGGGAT- GCTAGCGCATTTACAGC-3' (SEQ ID NO; 47), and cloned the product into pGL3 basic vector (pGL3-Nkx2.8-wtZBE). Mutant reporter plasmids (pGL3-Nkx2.8-mutZBE) were prepared by replacing the ZNFN3A1-binding sequences (CCCTCCT to CCGACCT and GAGGGG to GTCGGG) in pGL3-Nkx2.8-wtZBE using the QuickChange Site-Directed Mutagenesis Kit according to the supplier's recommendations (Stratagene). Luciferase assays were carried out using a Dual-Luciferase Reporter Assay System according to the manufacturer's instructions (Promega).

Establishment of HEK293-Nkx2.8Luc Cells.

Stable transformant of HEK293-Nkx2.8Luc cells were established by the transfection with pGL3-Nkx2.8-wtZBE and pcDNA(+)3.1 plasmids (10:1) into HEK293 cells using FuGENE6 reagent according to the supplier's recommendations (Roche). Transfected cells were maintained in culture media supplemented with 0.9 μg/μl of geneticin, and single colonies were selected two weeks after transfection.

Cell Lines

Human embryonic kidney 293 (HEK293) and human cervical cancer (HeLa) cells were obtained from IWAKI. A human hepatoma cell line HepG2, a human cervical cancer line HeLa, and a human colon cancer line HCT116 were obtained from the American Type Culture Collection (ATCC). Another human hepatoma cell line Huh7 was obtained from Japanese Collection of Research Bioresources (JCRB), while SNU423 and SNU475 were obtained from the Korea cell-line bank. All cell lines were grown in monolayers in appropriate media.

RT-PCR

Standard RT-PCR was carried out in a 20 μl volume of PCR buffer (TAKARA), and amplified for 4 min at 94° C. for denaturing, followed by 30 cycles of 94° C. for 30 s, 56° C. for 30 s, 72° C. for 30 s, in the Gene Amp PCR system 9700 (Perkin-Elmer). Primer sequences used for the RT-PCR experiments were shown in table 2.

TABLE 2

| Primers used for RT-PCR | | | SEQ ID No; |
|---|---|---|---|
| GAPDH; | F: | 5'-ACAACAGCCTCAAGATCATCAG-3' | 1 |
| | R: | 5'-GGTCCACCACTGACACGTTG-3' | 2 |

TABLE 2-continued

| Primers used for RT-PCR | | | SEQ ID No; |
|---|---|---|---|
| ZNFN3A1; | F: | 5'-TTCCCGATATCAACATCTACCAG-3' | 3 |
| | R: | 5'-AGTGTGTGACCTCAATAAGGCAT-3' | 4 |
| Nkx2.8; | F: | 5'-AATCATCGCTACAAGCTGAAGCGTG-3' | 5 |
| | R: | 5'-GCATAAAATCTAACTCTGGGGCTGG-3' | 6 |
| C/EBPδ, | F: | 5'-ACCTCTTCAACAGCAATCACAAG-3' | 7 |
| | R: | 5'-GCATGCTCAGTCTTTTCCTCTTA-3' | 8 |
| Nkx2.5; | F: | 5'-GTGCTCTTCTCGCAGGCGCAG-3' | 9 |
| | R: | 5'-ATACCATGCAGCGTGGACACTC-3' | 10 |
| Wnt10B; | F: | 5'-GATACCCACAACCGCAATTCT-3' | 11 |
| | R: | 5'-CAAACAGGAACCAAGAACAAGTC-3' | 12 |
| PIK3CB; | F: | 5'-AGTTAAACAGAGCCAAAGGGAAG-3' | 13 |
| | R: | 5'-CTGTAGTCTTTCCGAACTGTGTG-3' | 14 |
| NEURL; | F: | 5'-GAGACCATCTTCGTCAAGGTCACG-3' | 15 |
| | R: | 5'-CGTGTTCATAGCAAATGGTGCACTC-3' | 16 |
| PSMD9; | F: | 5'-CCCTTTGGAGAACAGGGAAAGCCTG-3' | 17 |
| | R: | 5'-GCTGATCTCAGGGCATAGCCAGGAG-3' | 18 |
| ECEL1; | F: | 5'-AAAGGCTGAGTGCATCGTCCGTCTC-3' | 19 |
| | R: | 5'-GGTAGCCAGCAGGAGGTGATTCGTG-3' | 20 |
| APS; | F: | 5'-AGAGAATCCCTGATCCACGTC-3' | 21 |
| | R: | 5'-CGGGCTAGTAGAAGGAGTACTGG-3' | 22 |
| Seb4D; | F: | 5'-GGCACCACTTTCGTGCAGTACCAGG-3' | 23 |
| | R: | 5'-GTCAGGCATCTCTGCACAGTCCAGG-3' | 24 |

Western Blot Analysis of Mutant Forms of ZNFN3A1.

Cells transfected with plasmids expressing wild type and various mutant forms of Flag-tagged ZNFN3A1 was immunoblotted with anti-ZNFN3A1 antibody or anti-Flag antibody. Plasmids expressing mutant forms of ZNFN3A1 were cloned into p3xFLAG-CMV-10 vector with PCR products amplified using sets of primers listed in Table 3.

TABLE 3

| Primers used for constructing mutant-type ZNFN3A1 | | | SEQ ID No; |
|---|---|---|---|
| p3xFlag-ZNFN3A1-Δ1; | F: | 5'-CGGAATTCTGGCGTCGTCTGCGACCGCTG-3' | 39 |
| | R: | 5'-GGGGTACCTTAGGATGCTCTGATGTTGGCGTC-3' | 40 |
| p3xFlag-ZNFN3A1-Δ2; | F: | 5'-CGGAATTCAGACTCCGTTCGACTTCTTGGCAG-3' | 41 |
| | R: | 5'-GGGGTACCTTAGGATGCTCTGATGTTGGCGTC-3' | 40 |
| p3xFlag-ZNFN3A1-Δ3; | F: | 5'-CGGAATTCCCGGAAGCAGCTGAGGGACCAGTAC-3' | 42 |
| | R: | 5'-GGGGTACCTTAGGATGCTCTGATGTTGGCGTC-3' | 40 |
| p3xFlag-ZNFN3A1-Δ4; | F: | 5'-CGGAATTCGATGGAGCCGCTGAAGGTGGAAAAG-3' | 43 |
| | R: | 5'-GGGGTACCTTACCGGCGCTCCTCACTGGTC-3' | 44 |
| p3xFlag-ZNFN3A1-Δ5; | F: | 5'-CGGAATTCGATGGAGCCGCTGAAGGTGGAAAAG-3' | 43 |
| | R: | 5'-GGGGTACCTTAGTCTGGAGGATATCTGGGTTTG-3' | 45 |

EXAMPLE 2

Determination of Methyl Transferase Activity of ZNFN3A1

Proteins containing the wild-type SET domain of ZNFN3A1 and two forms of mutant protein that lacked one of the two regions were prepared, and cross-linked equal amount of each protein with [$^3$H]-labeled SAM by exposure to UV-radiation. As shown in FIG. 1b, the wild-type SET domain was capable of interacting with [$^3$H]-labeled SAM and that neither of the mutants interacted with it, indicating the interaction of the SET domain with the methyl donor. The wild-type SET or control recombinant protein of SET7 was further incubated with [$^3$H]-labeled SAM and a mixture of histones as substrates, and labeled protein after the separation on SDS-PAGE was measured. As expected, a strong band corresponding to [$^3$H]-labeled histone H3 protein by the control SET7 (FIG. 1c, lane 3) was detected. When substrates were incubated with the wild-type SET of ZNFN3A1, a faint band corresponding to labeled histone H3 was detected, which was not observed with mock (FIG. 1c, lane 1 and 2).

Since yeast two-hybrid screening identified HSP90A as an interacting protein of ZNFN3A1, it was hypothesized that HSP90A might assist the protein folding of the SET. To test this hypothesis SAM and histones were incubated in combination with the wild-type SET and recombinant HSP90A protein, which resulted in enhanced methyl transferase activity onto histone H3 (FIG. 1c, lane 4 and 5). These data demonstrate that ZNFN3A1 regulates expression of downstream genes through modification of chromatin structure and the associated RNA polymerase II activity.

EXAMPLE 3

Histone H3 Methyltransferase Activity of ZNFN3A1

Since proteins containing SET domain play a crucial role in methylation of histone H3 lysine 4 (H3-K4) or lysine 9 (H3-K9), we investigated whether ZNFN3A1 has an ability to methylate H3-K4 or H3-K9. We incubated recombinant histone H3 in the presence of SAM and HSP90A with wild-type or mutant ZNFN3A1, or SET7 in vitro. In agreement with previous reports (26), SET7 enhanced mono- and di-methylation of H3-K4, but did not induce its tri-methylation (FIG. 2a, lane 2). On the other hand, the wild-type ZNFN3A1 did not lead to mono-methylation. However, it could cause di- and tri-methylation of H3-K4 (FIG. 2a, lane 3). This methylation was completely inhibited by addition of di-methylated H3-K4 peptides, but was unaffected by that of di-methylated H3-K9 peptides (FIG. 2b). The experiment using H3-K9 indicated that H3-K9 was methylated by neither wild-type nor mutant ZNFN3A1 (FIG. 2c), suggesting that ZNFN3A1 has the H3-K4-specific methyltransferase activity.

EXAMPLE 4

Histone H3-K4 Methyltransferase Activity of Recombinant ZNFN3A1

In addition, the entire coding region of wild type or mutant ZNFN3A1 was cloned into an appropriate cloning site of pGEX6P-1 vector, and expressed in the DH10B cells. Recombinant GST-ZNFN3A1 fusion protein was purified with Sepharose 4B beads (Amersham), and recombinant ZNFN3A1 was further separated using Precision protease (Amersham) according to the supplier's protocols (FIG. 3a, lane 4). The recombinant ZNFN3A1 also showed an HMTase activity to histone H3 in vitro (FIG. 3b). Western blot analysis using anti-di-methylated and anti-tri-methylated H3-K4 antibodies confirmed that the recombinant ZNFN3A1 induced di-methylation and tri-methylation on histone H3-K4 (FIG. 3c, upper and lower panel, respectively). Since S-adenosyl homocysteine hydrolase (SAHH) hydrolyzes SAH that is catalyzed from SAM and inhibits methylation, and enhances the methyltransferase activity (4), we have investigated whether SAHH affect on the histone H3 methyltransferase activity of ZNFN3A1. The H3 methyltransferase activity of Flag-tagged ZNFN3A1 was significantly higher in the presence of SAHH than the absence of SAHH (FIG. 3d).

EXAMPLE 5

Association Between HMTase Activity of ZNFN3A1 and Proliferation of Cancer Cells To analyze the effect of HMTase activity on cell growth, we carried out a colony-formation assay by transfecting plasmids expressing wild-type (p3xFLAG-CMV-ZNFN3A1) or HMTase-inactive mutant forms (p3xFLAG-CMV-ZNFN3A1-ΔEEL, p3xFLAG-CMV-ZNFN3A1-ΔNHSC) of ZNFN3A1, or control plasmids (p3xFLAG-CMV). Transduction of wild-type ZNFN3A1 produced markedly more colonies than control or mutant ZNFN3A1 in HEK293 cells expressing no endogenous ZNFN3A1, which recapitulated oncogenic activity of ZNFN3A1 (FIG. 4a). Consistently, transfection with p3xFLAG-CMV-ZNFN3A1 increased the number of colonies compared to the control in HCT116 colon cancer cells (FIG. 4b). On the other hand, that with p3xFLAG-CMV-ZNFN3A1-ΔEEL reduced the growth of HCT116 cells compared with p3xFLAG-CMV, suggesting that the mutant ZNFN3A1 may interfere the function of endogeneous ZNFN3A1. Additionally, we also investigated growth inhibitory effect of the mutant forms of plasmids in various colorectal cancer cell lines and hepatoma cell lines (FIG. 5). The result showed that transduction of HMTase-inactive ZNFN3A1 (p3xFLAG-CMV-ZNFN3A1-ΔEEL, p3xFLAG-CMV-ZNFN3A1-ΔNHSC) significantly reduced the growth of cancer cells compared to the control, which may suggest that HMTase activity of ZNFN3A1 associates with proliferation of colon cancer and hepatoma cells.

EXAMPLE 6

Identification of Genes Regulated by ZNFN3A1

To identify downstream genes regulated by ZNFN3A1, pcDNA-ZNFN3A1 was transfected into HEK293 cells that showed undetectable level of ZNFN3A1 expression by RT-PCR, and monitored alterations in gene expression using cDNA microarray containing 13,824 genes. Immunoblot analysis depicted time-dependent induction of ZNFN3A1 as early as 12 hours (FIG. 6a), therefore RNA was extracted from cells transfected with pcDNA-ZNFN3A1 and those with pcDNA-mock at 18 hours after transfection. The expression profile analysis identified 81 genes with altered expression including 62 genes that were up-regulated greater than three fold in pcDNA-ZNFN3A1 transfected cells compared with mock transfected cells, and 19 genes that were down-regulated less than three fold (Table 5). Among the 62 up-regulated genes, a set of oncogenes such as Myc, Crk, JunD, Maf, and Wnt10B, genes involved in cell cycle regulation (cyclin G1, Cdk2 and Topoisomerase II), and homeobox genes (Nkx2.5, Nkx2.8 and LIM homeobox protein 2) were found to be up-regulated by introduction of ZNFN3A1. Associated with cyclinA and cyclinE, cdk2 plays an crucial role for S-phase progression (5, 6), and the amplification of cyclinE/cdk2 complexes was shown to be involved in tumor progression in several tumors including CRC and HCC (7, 8). It is well known that homeobox genes are important factors for morphological change in development and for tumorigenesis (9). Therefore elevated expression of ZNFN3A1 plays a crucial role in human carcinogenesis through the activation of these downstream genes.

11 up-regulated genes including Nkx2.8, C/EBPδ, Nkx2.5, Wnt10B, PIK3CB, NEURL, PSMD9, ECEL1, CRKL, APS, and Seb4D were selected, and semi-quantitative RT-PCR was performed using RNA from the cells transfected with ZNFN3A1 or mock. The sets of primers used for semi-quantitative RT-PCR were shown in Table 2.

Expectedly, the result corroborated enhanced expression of these genes by ZNFN3A1 (FIG. 6b). The putative ZNFN3A1-binding sequences were searched within 1.5-kb region upstream of transcription starting sites of Nkx2.8. Two sequences were identified (FIG. 7a). Subsequent chromatin immunoprecipitation (CUP) assay using cells transfected with pFLAG-ZNFN3A1 and anti-Flag M2 antibody confirmed that one genomic segment (ChIP-4) containing these sequences associated with ZNFN3A1, and that other segments (ChIP-1, -2, and -3) with no ZNFN3A1-binding sequences did not (FIG. 7b). The ChIP-4 segment contained two putative binding sequences (CCCTCCT and GAGGGG) within −510 bp to −467 bp of the 5' flanking region (FIG. 7a). Double stranded oligonucleotide probe was prepared containing this ZNFN3A1-binding element (ZBE), and in vitro binding assay was performed, using recombinant GST, GST-ZNFN3A1, and GST-wtTcf4 as a control (FIG. 7c). The probe used for in vitro binding assay are shown in Table 4.

TABLE 4

Oligonucleotides used for in vitro binding assay

| | | SEQ ID No; |
|---|---|---|
| ZBE2; | F: 5'-TTACGCCCTCCTGAAACTTGT CATCCTGAATCTTAGAGGGGCCC-3' | 33 |
| | R: 5'-GGGCCCCTCTAAGATTCAGGA TGACAAGTTTCAGGAGGGCGTAA-3' | 34 |
| wtTBM; | F: 5'-CCCTTTGATCTTACC-3' | 35 |
| | R: 5'-GGTAAGATCAAAGGG-3' | 36 |
| mtTBM; | F: 5'-CCCTTTGGCCTTACC-3' | 37 |
| | R: 5'-GGTAAGGCCAAAGGG-3' | 38 |

The results indicate that oligonucleotide probe containing wild-type Tcf4-binding motif (wtTBM) associated with GST-wtTcf4 but not with GST or GST-ZNFN3A1 protein. Similarly, although ZBE did not associated with GST, it was capable to bind with GST-ZNFN3A1 protein. Furthermore, it was determined that the interaction was inhibited by the addition of cold competitor DNA, suggesting specific interaction between GST-ZNFN3A1 and ZBE.

TABLE 5

Up-regulated and down-regulated genes by ZNFN3A1

| Category | Unigene | Accession | Gene name |
|---|---|---|---|
| | | | Up-regulated genes |
| | | | Oncogene |
| 1 | Hs.25960 | BC002712 | V-myc myelocytomatosis viral related oncogene |
| 2 | Hs.5613 | NM_005207 | V-crk sarcoma virus CT10 oncogene homolog (avian)-like |
| 3 | Hs.2780 | X51346 | Jun D proto-oncogene |
| 4 | Hs.131953 | NM_002360 | V-maf musculoaponeurotic fibrosarcoma oncogene homolog K |
| 5 | Hs.91985 | NM_003394 | Wingless-type MMTV integration site family, member 10B |
| | | | Cell cycle |
| 6 | Hs.79101 | U47413 | Cyclin G1 |
| 7 | Hs.19192 | X62071 | Cyclin-dependent kinase 2 |
| 8 | Hs.75248 | U54831 | Topoisomerase (DNA) II beta |
| | | | Signal transduction |
| 9 | Hs.9195 | D21239 | Guanine nucleotide-releasing factor 2 |
| 10 | Hs.239818 | S67334 | Phosphoinositide-3-kinase, catalytic, beta polypeptide |
| 11 | Hs.89449 | L32976 | Mitogen-activated protein kinase kinase kinase 11 |
| 12 | Hs.418506 | BC026254 | Insulin-like 4 |
| 13 | Hs.21486 | NM_139266 | Signal transducer and activator of transcription 1 |
| 14 | Hs.31408 | NM_021168 | RAB40C, member RAS oncogene family |
| 15 | Hs.326392 | NM_005633 | Son of sevenless homolog 1 |
| 16 | Hs.371366 | NM_020979 | Adaptor protein with pleckstrin homology and src homology 2 domains (APS) |
| | | | Adhesion |
| 17 | Hs.138520 | AF057036 | Collagen-like tail subunit (single strand of homotrimer) of asymmetric acetylcholinesterase |
| 18 | Hs.81226 | U66142 | CD6 antigen |
| 19 | Hs.82848 | X16150 | Selectin L |
| 20 | Hs.149609 | W52075 | Integrin, alpha 5 |

TABLE 5-continued

Up-regulated and down-regulated genes by ZNFN3A1

| Category | Unigene | Accession | Gene name |
|---|---|---|---|
| 21 | Hs.78146 | M28526 | Platelet/endothelial cell adhesion molecule |
| 22 | Hs.172700 | U87864 | Neuralized-like |
| 23 | Hs.5302 | NM_006149 | Lectin, galactoside-binding, soluble, 4 |
|  |  |  | Receptor |
| 24 | Hs.123055 | U03865 | Adrenergic, alpha-1B-, receptor |
| 25 | Hs.123022 | J03853 | Adrenergic, alpha-2C-, receptor |
| 26 | Hs.418093 | XM_040709 | Prostaglandin F2 receptor negative regulator |
| 27 | Hs.26880 | AB030579 | Endothelin converting enzyme-like 1 |
|  |  |  | Morphology |
| 28 | Hs.54473 | U34962 | NK2 transcription factor related, locus 5 |
| 29 | Hs.234763 | NM_014360 | NK2 transcription factor related, locus 8 |
| 30 | Hs.1569 | AK027597 | LIM homeobox protein 2 |
| 31 | Hs.121539 | L38518 | Sonic hedgehog homolog |
|  |  |  | Transcription |
| 32 | Hs.147049 | L12579 | Cut-like 1, CCAAT displacement protein |
| 33 | Hs.42712 | M64240 | MAX protein |
| 34 | Hs.169832 | M58297 | Zinc finger protein 42 (myeloid-specific retinoic acid-responsive) |
| 35 | Hs.89657 | U13991 | TAF10 RNA polymerase II, TATA box binding protein (TBP)-associated factor, |
| 36 | Hs.76722 | M83667 | CCAAT/enhancer binding protein (C/EBP), delta |
| 37 | Hs.35841 | L31881 | Nuclear factor I/X (CCAAT-binding transcription factor) |
| 38 | Hs.130965 | AF309561 | Zinc-finger protein ZBRK1 |
| 39 | Hs.96028 | NM_004472 | Forkhead box D1 |
| 40 | Hs.22900 | AF125534 | Nuclear factor (erythroid-derived 2)-like 3 |
|  |  |  | Secreted |
| 41 | Hs.82963 | X01059 | Gonadotropin-releasing hormone 1 |
| 42 | Hs.821 | J04599 | Biglycan |
| 43 | Hs.1473 | K02054 | Gastrin-releasing peptide |
| 44 | Hs.148101 | BC009356 | CDC42 effector protein (Rho GTPase binding) 1 |
| 45 | Hs.11494 | NM_006329 | Fibulin 5 |
|  |  |  | Various enzyme |
| 46 | Hs.89512 | L20977 | ATPase, Ca++ transporting, plasma membrane 2 |
| 47 | Hs.170819 | AJ006701 | Serine/threonine kinase 29 |
| 48 | Hs.277445 | U94905 | Diacylglycerol kinase, zeta |
| 49 | Hs.75438 | X04882 | Quinoid dihydropteridine reductase |
| 50 | Hs.181046 | L05147 | Dual specificity phosphatase 3 |
| 51 | Hs.381034 | X78873 | Protein phosphatase 1, regulatory (inhibitor) subunit 2 |
| 52 | Hs.274376 | NM_004038 | Amylase, alpha 1A; salivary |
|  |  |  | Miscellaneous |
| 53 | Hs.11101 | U49089 | Discs, large (*Drosophila*) homolog 3 |
| 54 | Hs.43627 | NM_006943 | SRY (sex determining region Y)-box 12 |
| 55 | Hs.5648 | NM_002813 | Proteasome (prosome, macropain) 26S subunit, non-ATPase, 9 |
| 56 | Hs.343575 | U23435 | Abl-interactor 2 |
| 57 | Hs.124024 | AF053700 | Deltex homolog 1 |
| 58 | Hs.77492 | U23803 | Heterogeneous nuclear ribonucleoprotein A0 |
| 59 | Hs.635 | M76560 | Calcium channel, voltage-dependent, beta 1 subunit |
| 60 | Hs.279604 | AF055081 | Desmin |
| 61 | Hs.283429 | L25270 | Mcx homolog, X chromosom |
| 62 | Hs.236361 | BC018711 | RNA-binding region (RNP1, RRM) containing 1 |
|  |  |  | Down-regulated genes |
|  |  |  | Cell cycle |
| 63 | Hs.82173 | U21847 | Transforming growth factor-beta-inducible early growth response protein 1 |
| 64 | Hs.279862 | W81124 | Cdk inhibitor p21 binding protein |
|  |  |  | Transcription |
| 65 | Hs.110637 | AF040714 | Homeo box A10 |
| 66 | Hs.54424 | X76930 | Hepatocyte nuclear factor 4, alpha |
| 67 | Hs.102402 | NM_006454 | MAX dimerization protein 4 |
| 68 | Hs.12940 | AK025236 | Zinc-fingers and homeoboxes 1 |
|  |  |  | Secreted |
| 69 | Hs.295944 | D29992 | Tissue factor pathway inhibitor 2 |

TABLE 5-continued

Up-regulated and down-regulated genes by ZNFN3A1

| Category | Unigene | Accession | Gene name |
|---|---|---|---|
| | | | Various enzyme |
| 70 | Hs.90011 | AK025514 | Adenylosuccinate synthase |
| 71 | Hs.904 | U84010 | Amylo-1, 6-glucosidase, 4-alpha-glucanotransferase |
| 72 | Hs.8248 | AK098395 | NADH dehydrogenase (ubiquinone) Fe—S protein 1 |
| 73 | Hs.198272 | NM_004546 | NADH dehydrogenase (ubiquinone) 1 beta subcomplex, 2 |
| 74 | Hs.295605 | AL832306 | Mannosidase, alpha, class 2A, member 2 |
| 75 | Hs.211571 | U36787 | Holocytochrome c synthase |
| 76 | Hs.4099 | X93207 | Nardilysin (N-arginine dibasic convertase) |
| | | | Miscellaneous |
| 77 | Hs.81564 | NM_002619 | Platelet factor 4 |
| 78 | Hs.77770 | D38293 | Adaptor-related protein complex 3, mu 2 subunit |
| 70 | Hs.693 | M85085 | Cleavage stimulation factor, 3' pre-RNA, subunit 2 |
| 80 | Hs.422986 | M19383 | Annexin A4 |
| 81 | Hs.123122 | X97249 | FSH primary response (LRPR1 homolog, rat) 1 |

EXAMPLE 7

ZNFN3A1 Regulates Transcriptional Activity of Nkx2.8

To examine whether ZBE is responsible for transactivation of Nkx2.8 in cancer cells, a reporter plasmid was prepared that was cloned the −791 to +109 of Nkx2.8 including wild-type ZBE (pGL3-Nkx2.8-wtZBE) at an upstream region of luciferase gene as well as that including mutant ZBE (pGL3-Nkx2.8-mutZBE). These reporter plasmids were transfected into HepG2 or SNU475 cells, and their luciferase activity in the presence or absence of siRNA to ZNFN3A1 was measured (FIG. 7d). The mutant reporter plasmid revealed significantly lower activity than the wild-type plasmid in the cells, indicating that ZBE is responsible for the transactivation of Nkx2.8 in the cells. Notably, co-transfection with plasmids expressing siRNA to ZNFN3A1 (psiU6BX-ZNFN3A1-12 were prepared by cloning the following double stranded oligonucleotide into the Bbs1 site of the psiU6BX vector; Forward: 5'-CACCAACATCTACCAGCTGAAGGT-GTTCAAGAGACACCTTCAGCTGGTAGATGT T-3'(SEQ ID NO; 48), Reverse: 5'-AAAAAACATCTACCAGCT-GAAGGTGTCTCTTGAACACCTTCAGCTGGTAGATGT T-3'(SEQ ID NO; 49) (WO2004/76623)) reduced the luciferase activity of wild-type reporter plasmids compared to mock (psiU6BX-Mock), but it did not affect the activity of mutant plasmids.

These data indicate that ZNFN3A1 directly regulates transcriptional activity of Nkx2.8 through the interaction to ZBE.

EXAMPLE 8

Nkx2.8 is Associated with HSP90A-Dependent HMTase Activity of ZNFN3A1

To determine whether HMTase activity of ZNFN3A1 associates with the expression of Nkx2.8, and whether HSP90A is involved in its regulation, HEK293 cells were transfected with plasmids expressing wild-type or HMTase-inactive mutant-ZNFN3A1 (ZNFN3A1-ΔEEL and ZNFN3A1-ΔNHSC), and semi-quantitative RT-PCR was performed using RNAs isolated from the transfected cells (FIG. 7e). As expected, although wild-type plasmid enhanced the expression of Nkx8, both types of mutant plasmids failed to induce the expression. Furthermore, addition of geldanamycin, a specific inhibitor of HSP90A, suppressed the expression enhancement caused by wild-type ZNFN3A1 (FIG. 7e lane 3), which is consistent with the finding that HSP90A enhances HMTase activity of ZNFN3A1 in vitro (FIG. 1c). HEK293-Nkx2.8Luc cells that integrated the promoter region of Nkx2.8 and luciferase gene (pGL3-Nkx2.8-wtZBE) in the genome were established. Transfection with plasmids expressing wild-type ZNFN3A1 increased the luciferase activity in a dose-dependent manner, whereas, that in addition of 2 µM geldanamycin or that with HMTase-inactive mutant did not enhance the activity (FIG. 7f). Taken together, these results indicate that expression of Nkx2.8 is associated with HSP90A-dependent HMTase activity of ZNFN3A1.

EXAMPLE 9

Association Between Chip-4 Region in the Nkx2.8 Promoter and ZNFN3A1

We carried out an additional ChIP assay with anti-ZNFN3A1 antibody using extracts from HepG2 or Huh7 hepatoma cells that abundantly expressed ZNFN3A1, which corroborated an interaction between endogenous ZNFN3A1 protein and the ChIP-4 region (FIG. 8a). Further ChIP assay with anti-di-methylated H3-K4 antibody revealed an association between di-methylated H3-K4 and the ChIP-4 region in HEK293 cells transfected with wild-type ZNFN3A1 (FIG. 8b).

INDUSTRIAL APPLICABILITY

The present inventors have shown that ZNFN3A1 has methyl transferase activity, and the suppression of the activity leads to inhibition of cell proliferation of cancer cells. Thus, agents that inhibit the methyl transferase activity or the binding of ZNFN3A1 and co-factor thereof prevent its activity have therapeutic utility as anti-cancer agents, particularly anti-cancer agents for the treatment of HCC or colorectal cancer.

It has been reported that the expression of ZNFN3A1 is up-regulated in HCC or colorectal cancer. Thus, the methods for detection of the methyltransferase activity of ZNFN3A1 according to the present invention is also useful for identification of these cancers. Specifically, cells showing higher methyltransferase activity compared to normal cells can be identified as cancer cells.

Furthermore, a modulator that regulates the methyltransferase activity of ZNFN3A1 is also useful for identification of the cancers. For example, such a modulator can be used to confirm whether the methyltransferase activity detected in a subject cell is derived from ZNFN3A1. Specifically, when the methyltransferase activity is modified (inhibited or enhanced) by the modulator, the activity is judged as not being false positive.

All patents, patent applications, and publications cited herein are incorporated by reference in their entirety. Furthermore, while the invention has been described in detail and with reference to specific embodiments thereof, it will be apparent to one skilled in the art that various changes and modifications can be made therein without departing from the spirit and scope of the invention.

REFERENCES

1. Strahl, B. D., Ohba, R., Cook, R. G., and Allis, C. D. Methylation of histone H3 at lysine 4 is highly conserved and correlates with transcriptionally active nuclei in Tetrahymena. Proc Natl Acad Sci USA, 96: 14967-14972, 1999.
2. Okabe, H., Satoh, S., Furukawa, Y., Kato, T., Hasegawa, S., Nakajima, Y., Yamaoka, Y., and Nakamura, Y. Involvement of PEG10 in human hepatocellular carcinogenesis through interaction with SIAH1. Cancer Res, 63: 3043-3048, 2003.
3. Lin, Y. M., Furukawa, Y., Tsunoda, T., Yue, C. T., Yang, K. C., and Nakamura, Y. Molecular diagnosis of colorectal tumors by expression profiles of 50 genes expressed differentially in adenomas and carcinomas. Oncogene, 21: 4120-4128, 2002.
4. Stockand, J. D., Al-Baldawi, N. F., Al-Khalili, O. K., Worrell, R. T., and Eaton, D. C. S-adenosyl-L-homocysteine hydrolase regulates aldosterone-induced Na+ transport. J Biol Chem, 274: 3842-3850, 1999.
5. Krek, W., Ewen, M. E., Shirodkar, S., Arany, Z., Kaelin, W. G., Jr., and Livingston, D. M. Negative regulation of the growth-promoting transcription factor E2F-1 by a stably bound cyclin A-dependent protein kinase. Cell, 78: 161-172, 1994.
6. Dynlacht, B. D., Flores, O., Lees, J. A., and Harlow, E. Differential regulation of E2F transactivation by cyclin/cdk2 complexes. Genes Dev, 8: 1772-1786, 1994.
7. Kitahara, K., Yasui, W., Kuniyasu, H., Yokozaki, H., Akama, Y., Yunotani, S., Hisatsugu, T., and Tahara, E. Concurrent amplification of cyclin E and CDK2 genes in colorectal carcinomas. Int J Cancer, 62: 25-28, 1995.
8. Li, K. K., Ng, I. O., Fan, S. T., Albrecht, J. H., Yamashita, K., and Poon, R. Y. Activation of cyclin-dependent kinases CDC2 and CDK2 in hepatocellular carcinoma. Liver, 22: 259-268, 2002.
9. Cillo, C. HOX genes in human cancers. Invasion Metastasis, 14: 38-49, 1994.
10. Nakamura, T., Mori, T., Tada, S., Krajewski, W., Rozovskaia, T., Wassell, R., Dubois, G., Mazo, A., Croce, C. M., and Canaani, E. ALL-1 is a histone methyltransferase that assembles a supercomplex of proteins involved in transcriptional regulation. Mol Cell, 10: 1119-1128, 2002.
11. So, C. W., Lin, M., Ayton, P. M., Chen, E. H., and Cleary, M. L. Dimerization contributes to oncogenic activation of MLL chimeras in acute leukemias. Cancer Cell, 4: 9-110, 2003.
12. Milne, T. A., Briggs, S. D., Brock, H. W., Martin, M. E., Gibbs, D., Allis, C. D., and Hess, J. L. MLL targets SET domain methyltransferase activity to Hox gene promoters. Mol Cell, 10: 1107-1117, 2002.
13. Huntsman, D. G., Chin, S. F., Muleris, M., Batley, S. J., Collins, V. P., Wiedemann, L. M., Aparicio, S., and Caldas, C. MLL2, the second human homolog of the *Drosophila trithorax* gene, maps to 19q13.1 and is amplified in solid tumor cell lines. Oncogene, 18: 7975-7984, 1999.
14. Varambally, S., Dhanasekaran, S. M., Zhou, M., Barrette, T. R., Kumar-Sinha, C., Sanda, M. G., Ghosh, D., Pienta, K. J., Sewalt, R. G., Otte, A. P., Rubin, M. A., and Chinnaiyan, A. M. The polycomb group protein EZH2 is involved in progression of prostate cancer. Nature, 419: 624-629, 2002.
15. Bracken, A. P., Pasini, D., Capra, M., Prosperini, E., Colli, E., and Helin, K. EZH2 is downstream of the pRB-E2F pathway, essential for proliferation and amplified in cancer. Embo J, 22: 5323-5335, 2003.
16. Kwon, T. et al. Mechanism of histone lysine methyl transfer revealed by the structure of SET7/9-AdoMet. Embo J 22, 292-303 (2003).

The invention claimed is:

1. A method of measuring methyl transferase activity of a polypeptide, said method comprising the steps of:
   a. contacting a polypeptide selected from the group consisting of:
      i. a polypeptide comprising the amino acid sequence of SEQ ID NO: 51 (ZNFN3A1); and
      ii. a polypeptide that comprises the amino acid sequence having at least about 95% identity to SEQ ID NO: 51 in which both of NHSCDPN (SEQ ID NO:52) and GEELTICY (SEQ ID NO:53) are conserved, wherein the polypeptide has a methyltransferase activity for histone H3;
   with a substrate to be methylated and a cofactor under conditions capable of methylation of the substrate;
   b. detecting the methylation level of the substrate; and
   c. measuring the methyl transferase activity by correlating the methylation level of step (b) with the methyl transferase activity.

2. The method of claim 1, wherein the substrate is a histone or the fragment thereof comprising an at least methylation region.

3. The method of claim 1, wherein the methylation region is a histone H3 lysine 4.

4. The method of claim 1, wherein the cofactor is a S-adenosyl-L-methionine.

5. The method of claim 1, wherein the condition capable of methylation of the substrate is provided in the existence of heat shock protein 90A (HSP90A).

6. The method of claim 1, wherein the polypeptide is contacted with the substrate and cofactor in the presence of an enhancing agent for the methylation.

7. The method of claim 6, wherein the enhancing agent for the methylation is S-adenosyl homocysteine hydrolase (SAHH).

8. A method identifying an agent that modulates methyl transferase activity, said method comprising the steps of:
   a. contacting a polypeptide selected from the group consisting of:
      i. a polypeptide comprising the amino acid sequence of SEQ ID NO: 51; and
      ii. a polypeptide that comprises the amino acid sequence having at least about 95% identity to SEQ ID NO: 51 in which both of NHSCDPN (SEQ ID NO:52) and GEELTICY (SEQ ID NO:53) are conserved, wherein the polypeptide has a methyltransferase activity for histone H3;
   with a substrate to be methylated and a cofactor in the presence of a test compound under conditions capable of methylation of the substrate;
   b. detecting the methylation level of the substrate; and
   c. comparing the methylation level to a control level wherein an increase or decrease in the methylation level compared to control level indicates that the test compound modulates methyl transferase activity.

9. A kit for detecting an activity of a test compound to regulate methyl transferase activity, said kit comprising the components of:
   a. a polypeptide selected from the group consisting of:
      i. a polypeptide comprising the amino acid sequence of SEQ ID NO: 51; and
      ii. a polypeptide that comprises the amino acid sequence having at least about 95% identity to SEQ ID NO: 51 in which both of NHSCDPN (SEQ ID NO:52) and GEELTICY (SEQ ID NO:53) are conserved, wherein the polypeptide has a methyltransferase activity for histone H3,
   b. a substrate capable of methylation by the polypeptide of (a),
   c. a cofactor for the methylation of the substrate, and
   d. HSP90A.

10. The kit of claim 9, wherein the substrate is a histone or the fragment thereof comprising an at least methylation region.

11. The kit of claim 9, wherein said kit further comprises the element of:
   e. S-adenosyl homocysteine hydrolase (SAHH).

12. A method of screening for a compound for treating colorectal cancer or hepatocellular carcinoma, said method comprising the steps of:
   a. identifying the compound having an activity to modulate methyl transferase activity by the method of claim 7, and
   b. selecting a compound that decreases the methylation level of the substrate compared to a control level.

13. A method of screening for a compound for treating colorectal cancer or hepatocellular carcinoma, said method comprising the steps of:
   a. contacting a polypeptide selected from the group consisting of:
      i. a polypeptide comprising the amino acid sequence of SEQ ID NO: 51; and
      ii. a polypeptide that comprises the amino acid sequence having at least about 95% identity to SEQ ID NO: 51 in which both of NHSCDPN (SEQ ID NO:52) and GEELTICY (SEQ ID NO:53) are conserved, wherein the polypeptide has a binding activity to a heat shock protein 90A polypeptide (HSP90A);
   with a heat shock protein 90A polypeptide (HSP90A) in the presence of a test compound;
   b. detecting binding between the polypeptide and HSP90A;

c. comparing the binding of the polypeptide and HSP90A in the presence of the test compound with that in the absence of the test compound, and
d. selecting a test compound which decreases the binding of the polypeptide and HSP90A.

14. A kit for screening for a compound for treating colorectal cancer or hepatocellular carcinoma, said kit comprising the components of:
   a. a polypeptide selected from the group consisting of:
      i. a polypeptide comprising the amino acid sequence of SEQ ID NO: 51; and
      ii. a polypeptide that comprises the amino acid sequence having at least about 95% identity to SEQ ID NO: 51 in which both of NHSCDPN (SEQ ID NO:52) and GEELTICY (SEQ ID NO:53) are conserved, wherein the polypeptide has a binding activity to a heat shock protein 90A polypeptide (HSP90A); and
   b. HSP90A.

15. A method of screening for a compound for treating colorectal cancer or hepatocellular carcinoma, said method comprising the steps of:
   a. contacting a polypeptide comprising the amino acid sequence of SEQ ID NO: 51 or a polypeptide that comprises an amino acid sequence having at least about 95% identity to SEQ ID NO: 51, in which both of NHSCDPN (SEQ ID NO:52) and GEELTICY (SEQ ID NO:53) are conserved, and wherein the polypeptide binds to S-adenosyl-L-methionine, with an S-adenosyl-L-methionine in the presence of a test compound;
   b. detecting binding between the polypeptide and S-adenosyl-L-methionine;
   c. comparing the binding of the polypeptide and S-adenosyl-L-methionine in the presence of the test compound with that in the absence of the test compound, and
   d. selecting a test compound which decreases the binding between the polypeptide and S-adenosyl-L-methionine.

16. A kit for screening for a compound for treating colorectal cancer or hepatocellular carcinoma, said kit comprising the components of:
   a. a polypeptide comprising the amino acid sequence of SEQ ID NO: 51 or a polypeptide that comprises an amino acid sequence having at least about 95% identity to SEQ ID NO: 51 in which both of NHSCDPN (SEQ ID NO:52) and GEELTICY (SEQ ID NO:53) are conserved, and wherein the polypeptide binds to S-adenosyl-L-methionine; and
   b. S-adenosyl-L-methionine.

* * * * *

SEQUENCE LISTING

```
<160> NUMBER OF SEQ ID NOS: 55

<210> SEQ ID NO 1
<211> LENGTH: 22
<212> TYPE: DNA
<213> ORGANISM: Artificial
<220> FEATURE:
<223> OTHER INFORMATION: An artificially synthesized primer sequence for
      RT-PCR

<400> SEQUENCE: 1
acaacagcct caagatcatc ag                                              22

<210> SEQ ID NO 2
<211> LENGTH: 20
<212> TYPE: DNA
<213> ORGANISM: Artificial
```

```
<220> FEATURE:
<223> OTHER INFORMATION: An artificially synthesized primer sequence for
      RT-PCR

<400> SEQUENCE: 2
ggtccaccac tgacacgttg                                              20

<210> SEQ ID NO 3
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 3
ttcccgatat caacatctac cag                                          23

<210> SEQ ID NO 4
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 4
agtgtgtgac ctcaataagg cat                                          23

<210> SEQ ID NO 5
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 5
aatcatcgct acaagctgaa gcgtg                                        25

<210> SEQ ID NO 6
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 6
gcataaaatc taactctggg gctgg                                        25

<210> SEQ ID NO 7
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 7
acctcttcaa cagcaatcac aag                                          23

<210> SEQ ID NO 8
<211> LENGTH: 23
<212> TYPE: DNA
<213> ORGANISM: Artificial
<220> FEATURE:
<223> OTHER INFORMATION: An artificially synthesized primer sequence for
```

```
                                          RT-PCR

<400> SEQUENCE: 8
gcatgctcag tcttttcctc tta                                              23

<210> SEQ ID NO 9
<211> LENGTH: 21
<212> TYPE: DNA
<213> ORGANISM: Artificial
<220> FEATURE:
<223> OTHER INFORMATION: An artificially synthesized primer sequence for
      RT-PCR

<400> SEQUENCE: 9
gtgctcttct cgcaggcgca g                                                21

<210> SEQ ID NO 10
<211> LENGTH: 22
<212> TYPE: DNA
<213> ORGANISM: Artificial
<220> FEATURE:
<223> OTHER INFORMATION: An artificially synthesized primer sequence for
      RT-PCR

<400> SEQUENCE: 10
ataccatgca gcgtggacac tc                                               22

<210> SEQ ID NO 11
<211> LENGTH: 21
<212> TYPE: DNA
<213> ORGANISM: Artificial
<220> FEATURE:
<223> OTHER INFORMATION: An artificially synthesized primer sequence for
      RT-PCR

<400> SEQUENCE: 11
gatacccaca accgcaattc t                                                21

<210> SEQ ID NO 12
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 12
caaacaggaa ccaagaacaa gtc                                              23

<210> SEQ ID NO 13
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 13
agttaaacag agccaaaggg aag                                              23

<210> SEQ ID NO 14
<211> LENGTH: 23
<212> TYPE: DNA
<213> ORGANISM: Artificial
<220> FEATURE:
<223> OTHER INFORMATION: An artificially synthesized primer sequence for
      RT-PCR
```

<400> SEQUENCE: 14
ctgtagtctt tccgaactgt gtg                                          23

<210> SEQ ID NO 15
<211> LENGTH: 24
<212> TYPE: DNA
<213> ORGANISM: Artificial
<220> FEATURE:
<223> OTHER INFORMATION: An artificially synthesized primer sequence for
      RT-PCR

<400> SEQUENCE: 15
gagaccatct tcgtcaaggt cacg                                         24

<210> SEQ ID NO 16
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 16
cgtgttcata gcaaatggtg cactc                                        25

<210> SEQ ID NO 17
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 17
ccctttggag aacagggaaa gcctg                                        25

<210> SEQ ID NO 18
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 18
gctgatctca gggcatagcc aggag                                        25

<210> SEQ ID NO 19
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 19
aaaggctgag tgcatcgtcc gtctc                                        25

<210> SEQ ID NO 20
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 20

-continued ggtagccagc aggaggtgat tcgtg                                    25

<210> SEQ ID NO 21
<211> LENGTH: 21
<212> TYPE: DNA
<213> ORGANISM: Artificial
<220> FEATURE:
<223> OTHER INFORMATION: An artificially synthesized primer sequence for
      RT-PCR

<400> SEQUENCE: 21
agagaatccc tgatccacgt c                                        21

<210> SEQ ID NO 22
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 22
cgggctagta gaaggagtac tgg                                      23

<210> SEQ ID NO 23
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 23
ggcaccactt tcgtgcagta ccagg                                    25

<210> SEQ ID NO 24
<211> LENGTH: 25
<212> TYPE: DNA
<213> ORGANISM: Artificial
<220> FEATURE:
<223> OTHER INFORMATION: An artificially synthesized primer sequence for
      RT-PCR

<400> SEQUENCE: 24
gtcaggcatc tctgcacagt ccagg                                    25

<210> SEQ ID NO 25
<211> LENGTH: 26
<212> TYPE: DNA
<213> ORGANISM: Artificial
<220> FEATURE:
<223> OTHER INFORMATION: An artificially synthesized primer sequence for
      ChIP assay

<400> SEQUENCE: 25
tgcattattc cggactgaac aaatgc                                   26

<210> SEQ ID NO 26
<211> LENGTH: 25
<212> TYPE: DNA
<213> ORGANISM: Artificial
<220> FEATURE:
<223> OTHER INFORMATION: An artificially synthesized primer sequence for
      ChIP assay

<400> SEQUENCE: 26
gttgctaaat tgtagcgaag ggctc                                    25

-continued

```
<210> SEQ ID NO 27
<211> LENGTH: 25
<212> TYPE: DNA
<213> ORGANISM: Artificial
<220> FEATURE:
<223> OTHER INFORMATION: An artificially synthesized primer sequence for
      ChIP assay

<400> SEQUENCE: 27
acccaagtac agagcccttc gctac                                          25

<210> SEQ ID NO 28
<211> LENGTH: 24
<212> TYPE: DNA
<213> ORGANISM: Artificial
<220> FEATURE:
<223> OTHER INFORMATION: An artificially synthesized primer sequence for
      ChIP assay

<400> SEQUENCE: 28
tcactgcctg ggctttggtc tttg                                           24

<210> SEQ ID NO 29
<211> LENGTH: 25
<212> TYPE: DNA
<213> ORGANISM: Artificial
<220> FEATURE:
<223> OTHER INFORMATION: An artificially synthesized primer sequence for
      ChIP assay

<400> SEQUENCE: 29
gaccaaagcc caggcagtga gagtg                                          25

<210> SEQ ID NO 30
<211> LENGTH: 25
<212> TYPE: DNA
<213> ORGANISM: Artificial
<220> FEATURE:
<223> OTHER INFORMATION: An artificially synthesized primer sequence for
      ChIP assay

<400> SEQUENCE: 30
ctgaggaagg gctgggacaa cattc                                          25

<210> SEQ ID NO 31
<211> LENGTH: 25
<212> TYPE: DNA
<213> ORGANISM: Artificial
<220> FEATURE:
<223> OTHER INFORMATION: An artificially synthesized primer sequence for
      ChIP assay

<400> SEQUENCE: 31
tggctacaag cctcttctgt tttgc                                          25

<210> SEQ ID NO 32
<211> LENGTH: 25
<212> TYPE: DNA
<213> ORGANISM: Artificial
<220> FEATURE:
<223> OTHER INFORMATION: An artificially synthesized primer sequence for
      ChIP assay

<400> SEQUENCE: 32
aggggtgggt ttattagcac ccagg                                          25

<210> SEQ ID NO 33
```

-continued

```
<211> LENGTH: 44
<212> TYPE: DNA
<213> ORGANISM: Artificial
<220> FEATURE:
<223> OTHER INFORMATION: An artificially synthesized oligonucleotide
      probe for in vitro binding assay

<400> SEQUENCE: 33
ttacgccctc ctgaaacttg tcatcctgaa tcttagaggg gccc                    44

<210> SEQ ID NO 34
<211> LENGTH: 44
<212> TYPE: DNA
<213> ORGANISM: Artificial
<220> FEATURE:
<223> OTHER INFORMATION: An artificially synthesized oligonucleotide
      probe for in vitro binding assay

<400> SEQUENCE: 34
gggcccctct aagattcagg atgacaagtt tcaggagggc gtaa                    44

<210> SEQ ID NO 35
<211> LENGTH: 15
<212> TYPE: DNA
<213> ORGANISM: Artificial
<220> FEATURE:
<223> OTHER INFORMATION: An artificially synthesized oligonucleotide
      probe for in vitro binding assay

<400> SEQUENCE: 35
ccctttgatc ttacc                                                    15

<210> SEQ ID NO 36
<211> LENGTH: 15
<212> TYPE: DNA
<213> ORGANISM: Artificial
<220> FEATURE:
<223> OTHER INFORMATION: An artificially synthesized oligonucleotide
      probe for in vitro binding assay

<400> SEQUENCE: 36
ggtaagatca aaggg                                                    15

<210> SEQ ID NO 37
<211> LENGTH: 15
<212> TYPE: DNA
<213> ORGANISM: Artificial
<220> FEATURE:
<223> OTHER INFORMATION: An artificially synthesized oligonucleotide
      probe for in vitro binding assay

<400> SEQUENCE: 37
ccctttggcc ttacc                                                    15

<210> SEQ ID NO 38
<211> LENGTH: 15
<212> TYPE: DNA
<213> ORGANISM: Artificial
<220> FEATURE:
<223> OTHER INFORMATION: An artificially synthesized oligonucleotide
      probe for in vitro binding assay

<400> SEQUENCE: 38
ggtaaggcca aaggg                                                    15

<210> SEQ ID NO 39
<211> LENGTH: 29
<212> TYPE: DNA
```

-continued

<213> ORGANISM: Artificial
<220> FEATURE:
<223> OTHER INFORMATION: An artificially synthesized primer sequence for
      constructiing mutant-type ZNFN3A1.

<400> SEQUENCE: 39
cggaattctg gcgtcgtctg cgaccgctg                                      29

<210> SEQ ID NO 40
<211> LENGTH: 32
<212> TYPE: DNA
<213> ORGANISM: Artificial
<220> FEATURE:
<223> OTHER INFORMATION: An artificially synthesized primer sequence for
      constructiing mutant-type ZNFN3A1.

<400> SEQUENCE: 40
ggggtacctt aggatgctct gatgttggcg tc                                  32

<210> SEQ ID NO 41
<211> LENGTH: 32
<212> TYPE: DNA
<213> ORGANISM: Artificial
<220> FEATURE:
<223> OTHER INFORMATION: An artificially synthesized primer sequence for
      constructiing mutant-type ZNFN3A1.

<400> SEQUENCE: 41
cggaattcag actccgttcg acttcttggc ag                                  32

<210> SEQ ID NO 42
<211> LENGTH: 33
<212> TYPE: DNA
<213> ORGANISM: Artificial
<220> FEATURE:
<223> OTHER INFORMATION: An artificially synthesized primer sequence for
      constructiing mutant-type ZNFN3A1.

<400> SEQUENCE: 42
cggaattccc ggaagcagct gagggaccag tac                                 33

<210> SEQ ID NO 43
<211> LENGTH: 33
<212> TYPE: DNA
<213> ORGANISM: Artificial
<220> FEATURE:
<223> OTHER INFORMATION: An artificially synthesized primer sequence for
      constructiing mutant-type ZNFN3A1.

<400> SEQUENCE: 43
cggaattcga tggagccgct gaaggtggaa aag                                 33

<210> SEQ ID NO 44
<211> LENGTH: 30
<212> TYPE: DNA
<213> ORGANISM: Artificial
<220> FEATURE:
<223> OTHER INFORMATION: An artificially synthesized primer sequence for
      constructiing mutant-type ZNFN3A1.

<400> SEQUENCE: 44
ggggtacctt accggcgctc ctcactggtc                                     30

<210> SEQ ID NO 45
<211> LENGTH: 33
<212> TYPE: DNA
<213> ORGANISM: Artificial
<220> FEATURE:

```
<223> OTHER INFORMATION: An artificially synthesized primer sequence for
      constructiing mutant-type ZNFN3A1.

<400> SEQUENCE: 45
ggggtacctt agtctggagg atatctgggt ttg                                  33

<210> SEQ ID NO 46
<211> LENGTH: 24
<212> TYPE: DNA
<213> ORGANISM: Artificial
<220> FEATURE:
<223> OTHER INFORMATION: An artificially synthesized primer sequence to
      amplyfy the fragment of Nkx2.8 promoter by PCR

<400> SEQUENCE: 46
agcgggcctg gtaccaaatt tgtg                                            24

<210> SEQ ID NO 47
<211> LENGTH: 24
<212> TYPE: DNA
<213> ORGANISM: Artificial
<220> FEATURE:
<223> OTHER INFORMATION: An artificially synthesized primer sequence to
      amplyfy the fragment of Nkx2.8 promoter by PCR

<400> SEQUENCE: 47
ccgggatgct agcgcattta cagc                                            24

<210> SEQ ID NO 48
<211> LENGTH: 55
<212> TYPE: DNA
<213> ORGANISM: Artificial
<220> FEATURE:
<223> OTHER INFORMATION: An artificially synthesized oliginucleotide
      sequence for plasmids expressing siRNA to ZNFN3A1

<400> SEQUENCE: 48
caccaacatc taccagctga aggtgttcaa gagacacctt cagctggtag atgtt          55

<210> SEQ ID NO 49
<211> LENGTH: 55
<212> TYPE: DNA
<213> ORGANISM: Artificial
<220> FEATURE:
<223> OTHER INFORMATION: An artificially synthesized oliginucleotide
      sequence for plasmids expressing siRNA to ZNFN3A1

<400> SEQUENCE: 49
aaaaaacatc taccagctga aggtgtctct tgaacacctt cagctggtag atgtt          55

<210> SEQ ID NO 50
<211> LENGTH: 1622
<212> TYPE: DNA
<213> ORGANISM: Homo sapiens
<220> FEATURE:
<221> NAME/KEY: CDS
<222> LOCATION: (96)..(1382)

<400> SEQUENCE: 50
gtgcgcgcag ggcgcaggcg cgcgggtccc ggcagcccgt gagacgcccg ctgctggacg     60
cgggtagccg tctgaggtgc cggagctgcg ggagg atg gag ccg ctg aag gtg       113
                                     Met Glu Pro Leu Lys Val
                                       1               5 gaa aag ttc gca acc gcc aac agg gga aac ggg ctg cgc gcc gtg acc      161
Glu Lys Phe Ala Thr Ala Asn Arg Gly Asn Gly Leu Arg Ala Val Thr
         10                  15                  20
```

| | | |
|---|---|---|
| ccg ctg cgc ccc gga gag cta ctc ttc cgc tcg gat ccc ttg gcg tac<br>Pro Leu Arg Pro Gly Glu Leu Leu Phe Arg Ser Asp Pro Leu Ala Tyr<br>25                       30                     35 | 209 |
| acg gtg tgc aag ggg agt cgt ggc gtc gtc tgc gac cgc tgc ctt ctc<br>Thr Val Cys Lys Gly Ser Arg Gly Val Val Cys Asp Arg Cys Leu Leu<br>    40                     45                   50 | 257 |
| ggg aag gaa aag ctg atg cga tgc tct cag tgc cgc gtc gcc aaa tac<br>Gly Lys Glu Lys Leu Met Arg Cys Ser Gln Cys Arg Val Ala Lys Tyr<br>55                       60                            70 | 305 |
| tgt agt gct aag tgt cag aaa aaa gct tgg cca gac cac aag cgg gaa<br>Cys Ser Ala Lys Cys Gln Lys Lys Ala Trp Pro Asp His Lys Arg Glu<br>           75                   80                   85 | 353 |
| tgc aaa tgc ctt aaa agc tgc aaa ccc aga tat cct cca gac tcc gtt<br>Cys Lys Cys Leu Lys Ser Cys Lys Pro Arg Tyr Pro Pro Asp Ser Val<br>          90                   95                 100 | 401 |
| cga ctt ctt ggc aga gtt gtc ttc aaa ctt atg gat gga gca cct tca<br>Arg Leu Leu Gly Arg Val Val Phe Lys Leu Met Asp Gly Ala Pro Ser<br>        105                  110                  115 | 449 |
| gaa tca gag aag ctt tac tca ttt tat gat ctg gag tca aat att aac<br>Glu Ser Glu Lys Leu Tyr Ser Phe Tyr Asp Leu Glu Ser Asn Ile Asn<br>120                      125                  130 | 497 |
| aaa ctg act gaa gat aag aaa gag ggc ctc agg caa ctc gta atg aca<br>Lys Leu Thr Glu Asp Lys Lys Glu Gly Leu Arg Gln Leu Val Met Thr<br>135                     140                   145                  150 | 545 |
| ttt caa cat ttc atg aga gaa gaa ata cag gat gcc tct cag ctg cca<br>Phe Gln His Phe Met Arg Glu Glu Ile Gln Asp Ala Ser Gln Leu Pro<br>                155                  160                  165 | 593 |
| cct gcc ttt gac ctt ttt gaa gcc ttt gca aaa gtg atc tgc aac tct<br>Pro Ala Phe Asp Leu Phe Glu Ala Phe Ala Lys Val Ile Cys Asn Ser<br>            170                  175                  180 | 641 |
| ttc acc atc tgt aat gcg gag atg cag gaa gtt ggt gtt ggc cta tat<br>Phe Thr Ile Cys Asn Ala Glu Met Gln Glu Val Gly Val Gly Leu Tyr<br>        185                  190                  195 | 689 |
| ccc agt atc tct ttg ctc aat cac agc tgt gac ccc aac tgt tcg att<br>Pro Ser Ile Ser Leu Leu Asn His Ser Cys Asp Pro Asn Cys Ser Ile<br>200                      205                  210 | 737 |
| gtg ttc aat ggg ccc cac ctc tta ctg cga gca gtc cga gac atc gag<br>Val Phe Asn Gly Pro His Leu Leu Leu Arg Ala Val Arg Asp Ile Glu<br>215                     220                  225                  230 | 785 |
| gtg gga gag gag ctc acc atc tgc tac ctg gat atg ctg atg acc agt<br>Val Gly Glu Glu Leu Thr Ile Cys Tyr Leu Asp Met Leu Met Thr Ser<br>                235                  240                  245 | 833 |
| gag gag cgc cgg aag cag ctg agg gac cag tac tgc ttt gaa tgt gac<br>Glu Glu Arg Arg Lys Gln Leu Arg Asp Gln Tyr Cys Phe Glu Cys Asp<br>            250                  255                  260 | 881 |
| tgt ttc cgt tgc caa acc cag gac aag gat gct gat atg cta act ggt<br>Cys Phe Arg Cys Gln Thr Gln Asp Lys Asp Ala Asp Met Leu Thr Gly<br>        265                  270                  275 | 929 |
| gat gag caa gta tgg aag gaa gtt caa gaa tcc ctg aaa aaa att gaa<br>Asp Glu Gln Val Trp Lys Glu Val Gln Glu Ser Leu Lys Lys Ile Glu<br>280                      285                  290 | 977 |
| gaa ctg aag gca cac tgg aag tgg gag cag gtt ctg gcc atg tgc cag<br>Glu Leu Lys Ala His Trp Lys Trp Glu Gln Val Leu Ala Met Cys Gln<br>295                     300                  305                  310 | 1025 |
| gcg atc ata agc agc aat tct gaa cgg ctt ccc gat atc aac atc tac<br>Ala Ile Ile Ser Ser Asn Ser Glu Arg Leu Pro Asp Ile Asn Ile Tyr<br>                315                  320                  325 | 1073 |
| cag ctg aag gtg ctc gac tgc gcc atg gat gcc tgc atc aac ctc ggc<br>Gln Leu Lys Val Leu Asp Cys Ala Met Asp Ala Cys Ile Asn Leu Gly<br>            330                  335                  340 | 1121 |

```
ctg ttg gag gaa gcc ttg ttc tat ggt act cgg acc atg gag cca tac      1169
Leu Leu Glu Glu Ala Leu Phe Tyr Gly Thr Arg Thr Met Glu Pro Tyr
            345                 350                 355 agg att ttt ttc cca gga agc cat ccc gtc aga ggg gtt caa gtg atg      1217
Arg Ile Phe Phe Pro Gly Ser His Pro Val Arg Gly Val Gln Val Met
        360                 365                 370 aaa gtt ggc aaa ctg cag cta cat caa ggc atg ttt ccc caa gca atg      1265
Lys Val Gly Lys Leu Gln Leu His Gln Gly Met Phe Pro Gln Ala Met
375                 380                 385                 390 aag aat ctg aga ctg gct ttt gat att atg aga gtg aca cat ggc aga      1313
Lys Asn Leu Arg Leu Ala Phe Asp Ile Met Arg Val Thr His Gly Arg
                395                 400                 405 gaa cac agc ctg att gaa gat ttg att cta ctt tta gaa gaa tgc gac      1361
Glu His Ser Leu Ile Glu Asp Leu Ile Leu Leu Leu Glu Glu Cys Asp
            410                 415                 420 gcc aac atc aga gca tcc taa gggaacgcag tcagagggaa atacggcgtg         1412
Ala Asn Ile Arg Ala Ser
            425 tgtctttgtt gaatgcctta ttgaggtcac acactctatg ctttgttagc tgtgtgaacc    1472 tctcttattg gaaattctgt tccgtgtttg tgtaggtaaa taaaggcaga catggtttgc    1532 aaaccacaag aatcattagt tgtagagaag cacgattata ataaattcaa acatttggt    1592 tgaggatgcc aaaaaaaaaa aaaaaaaaa                                      1622

<210> SEQ ID NO 51
<211> LENGTH: 428
<212> TYPE: PRT
<213> ORGANISM: Homo sapiens

<400> SEQUENCE: 51

Met Glu Pro Leu Lys Val Glu Lys Phe Ala Thr Ala Asn Arg Gly Asn
1               5                   10                  15

Gly Leu Arg Ala Val Thr Pro Leu Arg Pro Gly Glu Leu Leu Phe Arg
            20                  25                  30

Ser Asp Pro Leu Ala Tyr Thr Val Cys Lys Gly Ser Arg Gly Val Val
        35                  40                  45

Cys Asp Arg Cys Leu Leu Gly Lys Glu Lys Leu Met Arg Cys Ser Gln
    50                  55                  60

Cys Arg Val Ala Lys Tyr Cys Ser Ala Lys Cys Gln Lys Lys Ala Trp
65                  70                  75                  80

Pro Asp His Lys Arg Glu Cys Lys Cys Leu Lys Ser Cys Lys Pro Arg
                85                  90                  95

Tyr Pro Pro Asp Ser Val Arg Leu Leu Gly Arg Val Val Phe Lys Leu
            100                 105                 110

Met Asp Gly Ala Pro Ser Glu Ser Glu Lys Leu Tyr Ser Phe Tyr Asp
        115                 120                 125

Leu Glu Ser Asn Ile Asn Lys Leu Thr Glu Asp Lys Lys Glu Gly Leu
    130                 135                 140

Arg Gln Leu Val Met Thr Phe Gln His Phe Met Arg Glu Glu Ile Gln
145                 150                 155                 160

Asp Ala Ser Gln Leu Pro Pro Ala Phe Asp Leu Phe Glu Ala Phe Ala
                165                 170                 175

Lys Val Ile Cys Asn Ser Phe Thr Ile Cys Asn Ala Glu Met Gln Glu
            180                 185                 190

Val Gly Val Gly Leu Tyr Pro Ser Ile Ser Leu Leu Asn His Ser Cys
        195                 200                 205

Asp Pro Asn Cys Ser Ile Val Phe Asn Gly Pro His Leu Leu Leu Arg
```

```
                210              215                 220
Ala Val Arg Asp Ile Glu Val Gly Glu Leu Thr Ile Cys Tyr Leu
225                 230                 235                 240

Asp Met Leu Met Thr Ser Glu Glu Arg Arg Lys Gln Leu Arg Asp Gln
                245                 250                 255

Tyr Cys Phe Glu Cys Asp Cys Phe Arg Cys Gln Thr Gln Asp Lys Asp
                260                 265                 270

Ala Asp Met Leu Thr Gly Asp Glu Gln Val Trp Lys Glu Val Gln Glu
                275                 280                 285

Ser Leu Lys Lys Ile Glu Glu Leu Lys Ala His Trp Lys Trp Glu Gln
290                 295                 300

Val Leu Ala Met Cys Gln Ala Ile Ile Ser Ser Asn Ser Glu Arg Leu
305                 310                 315                 320

Pro Asp Ile Asn Ile Tyr Gln Leu Lys Val Leu Asp Cys Ala Met Asp
                325                 330                 335

Ala Cys Ile Asn Leu Gly Leu Leu Glu Glu Ala Leu Phe Tyr Gly Thr
                340                 345                 350

Arg Thr Met Glu Pro Tyr Arg Ile Phe Phe Pro Gly Ser His Pro Val
                355                 360                 365

Arg Gly Val Gln Val Met Lys Val Gly Lys Leu Gln Leu His Gln Gly
370                 375                 380

Met Phe Pro Gln Ala Met Lys Asn Leu Arg Leu Ala Phe Asp Ile Met
385                 390                 395                 400

Arg Val Thr His Gly Arg Glu His Ser Leu Ile Glu Asp Leu Ile Leu
                405                 410                 415

Leu Leu Glu Glu Cys Asp Ala Asn Ile Arg Ala Ser
                420                 425

<210> SEQ ID NO 52
<211> LENGTH: 7
<212> TYPE: PRT
<213> ORGANISM: Homo sapiens

<400> SEQUENCE: 52

Asn His Ser Cys Asp Pro Asn
1               5

<210> SEQ ID NO 53
<211> LENGTH: 8
<212> TYPE: PRT
<213> ORGANISM: Homo sapiens

<400> SEQUENCE: 53

Gly Glu Glu Leu Thr Ile Cys Tyr
1               5

<210> SEQ ID NO 54
<211> LENGTH: 7
<212> TYPE: PRT
<213> ORGANISM: Homo sapiens
<220> FEATURE:
<221> NAME/KEY: MISC_FEATURE
<222> LOCATION: (5)..(6)
<223> OTHER INFORMATION: "Xaa" indicates any amino acid

<400> SEQUENCE: 54

Asn His Ser Cys Xaa Xaa Asn
1               5

<210> SEQ ID NO 55
```

-continued

```
<211> LENGTH: 8
<212> TYPE: PRT
<213> ORGANISM: Homo sapiens
<220> FEATURE:
<221> NAME/KEY: MISC_FEATURE
<222> LOCATION: (5)..(7)
<223> OTHER INFORMATION: "Xaa" indicates any amino acid

<400> SEQUENCE: 55

Gly Glu Glu Leu Xaa Xaa Xaa Tyr
1               5
```